United States Patent
Taguchi

(10) Patent No.: US 10,064,973 B2
(45) Date of Patent: Sep. 4, 2018

(54) TISSUE ADHESIVE AND METHOD FOR PRODUCING SAME

(71) Applicant: NATIONAL INSTITUTE FOR MATERIALS SCIENCE, Ibaraki (JP)

(72) Inventor: Tetsushi Taguchi, Ibaraki (JP)

(73) Assignee: National Institute for Materials Science, Ibaraki (JP)

(*) Notice: Subject to any disclaimer, the term of this patent is extended or adjusted under 35 U.S.C. 154(b) by 90 days.

(21) Appl. No.: 14/761,326

(22) PCT Filed: Nov. 22, 2013

(86) PCT No.: PCT/JP2013/081559
§ 371 (c)(1),
(2) Date: Jul. 16, 2015

(87) PCT Pub. No.: WO2014/112208
PCT Pub. Date: Jul. 24, 2014

(65) Prior Publication Data
US 2015/0359924 A1   Dec. 17, 2015

(30) Foreign Application Priority Data
Jan. 18, 2013 (JP) ................... 2013-006961

(51) Int. Cl.
*A61L 24/10* (2006.01)
(52) U.S. Cl.
CPC .................. *A61L 24/104* (2013.01)
(58) Field of Classification Search
CPC .................................................. A61L 24/104
See application file for complete search history.

(56) References Cited

U.S. PATENT DOCUMENTS 5,093,474 A * 3/1992 Grossman ............... C09H 3/00
                                                            426/576
6,833,408 B2 * 12/2004 Sehl ...................... A61L 24/043
                                                            424/422

(Continued)

FOREIGN PATENT DOCUMENTS

JP     09-103479      4/1997
JP     2008-104398    5/2008

(Continued)

OTHER PUBLICATIONS

Taguchi et al. "Biodegradable Adhesives Composed of Human Serum Albumin and Organic Acid-based Crosslinkers with Active Ester Group", Journal of Bioactive and Compatible Palymer, vol. 24, Nov. 2009.

(Continued)

*Primary Examiner* — Shuangyi Abu Ali
(74) *Attorney, Agent, or Firm* — Wenderoth, Lind & Ponack, L.L.P.

(57) ABSTRACT

There is provided a tissue adhesive to be applied to a tissue by mixing an adhesive component including an aqueous solution of a fish-derived gelatin with a curative component including an aqueous solution of a water-soluble crosslinking reagent, wherein the water-soluble crosslinking reagent has an amide linkage or an ethylene glycol unit or a sugar chain in the molecular main chain thereof and has two or more of an active ester group or an acid anhydride or an aldehyde group.

9 Claims, 29 Drawing Sheets

(56) References Cited

U.S. PATENT DOCUMENTS

| | | | |
|---|---|---|---|
| RE38,827 E * | 10/2005 | Barrows | A61L 24/043 |
| | | | 424/179.1 |
| 2006/0105026 A1 | 5/2006 | Fortune et al. | |
| 2013/0220174 A1 * | 8/2013 | Taguchi | C09J 189/00 |
| | | | 106/155.21 |

FOREIGN PATENT DOCUMENTS

| | | |
|---|---|---|
| JP | 2008-284256 | 11/2008 |
| JP | 2010-132770 | 6/2010 |
| WO | 9603159 | 2/1996 |
| WO | 2008/006545 | 1/2008 |
| WO | 2008/076407 | 6/2008 |

OTHER PUBLICATIONS

Lin et al., "Preparation and surface activity of gelatin derivative surfactants" Colloids and Surfaces A:Physicochem, Eng. Aspect 272 (2006) 8-14.

Lin et al., "The pH-Dependent Surface Properties of Gelatin-Alkenylsuccinic Acid Anhydride Derived Surfactants", Journal of Applied Polymer Science, vol. 105, 3371-3377 (2007).

Matsuda et al., "Enhanced tissue penetration-induced high bonding strength of a novel tissue adhesive composed of cholesteryl group-modified gelatin and disuccinimidyl tartarate", Colloids and Surfaces B:Biointerfaces 91 (2012) 48-56.

Dowling et al., "Sprayable Foams Based on an Amphiphilic Biopolymer for Control of Hemorrhage Without Compression", ACS Biomater, Sci. Eng. 2015, 1, 440-447.

Dowling et al., "A self-assembling hydrophobically modified chitosan capable of reversible hemostatic action", Biomaterials 32 (2011) 3351-3357.

Endo et al., "Development of Liquid-Liquid Tissue Adhesive possessing Tissue Penetration and Elastic Property", Proceedings of Medicine-Engineering Collaboration Forum Tsukuba 2013.

International Search Report dated Feb. 4, 2014 in International (PCT) Application No. PCT/JP2013/081559.

Tsunemi et al., "Changes of Fish Collagen by Chemical Modification and Enzymatic Cross Linkage", Reports of Saitama Industrial Technology Center, vol. 2, 2004, pp. 115-119.

* cited by examiner

F I G . 1
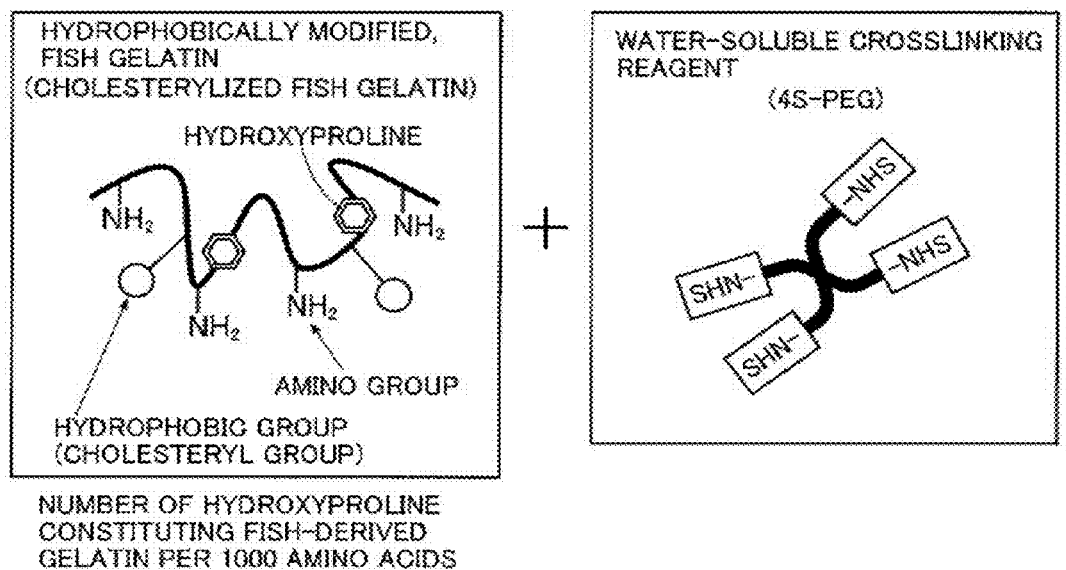

Image of cross-section stained with
hematoxylin and eosin
(Condition: Gltn 40wt% soln.
4S-PEG 4.5mM(0.1M PBS pH6.0))

Image of cross-section stained with hematoxylin and eosin
(Condition: Gltn 40wt% soln.
4S-PEG 4.5mM(0.1M PBS pH6.5))

F I G . 1 1
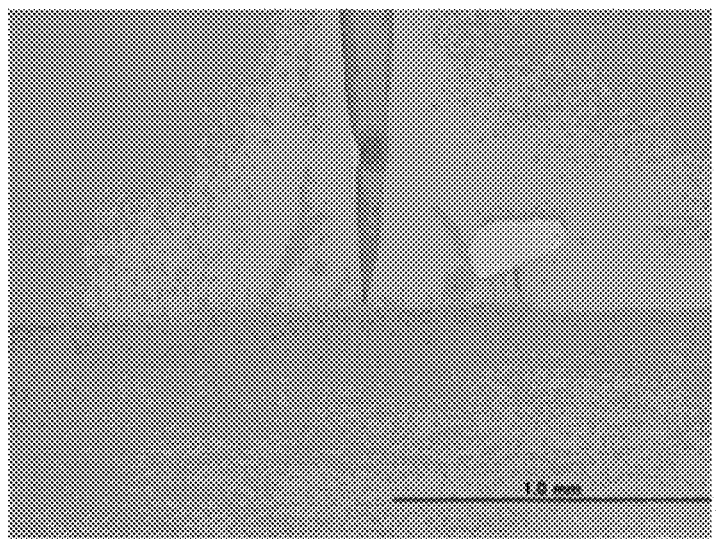
Image of cross-section stained with
hematoxylin and eosin
(Condition: Gltn 40wt% soln.
4S-PEG 4.5mM(0.1M PBS pH7.0))

Image of cross-section stained with
hematoxylin and eosin
(Condition: Gltn 40wt% soln.
4S-PEG 4.5mM(0.1M PBS pH7.5))

Image of cross-section stained with hematoxylin and eosin (Condition: GRF)

F I G . 1 6
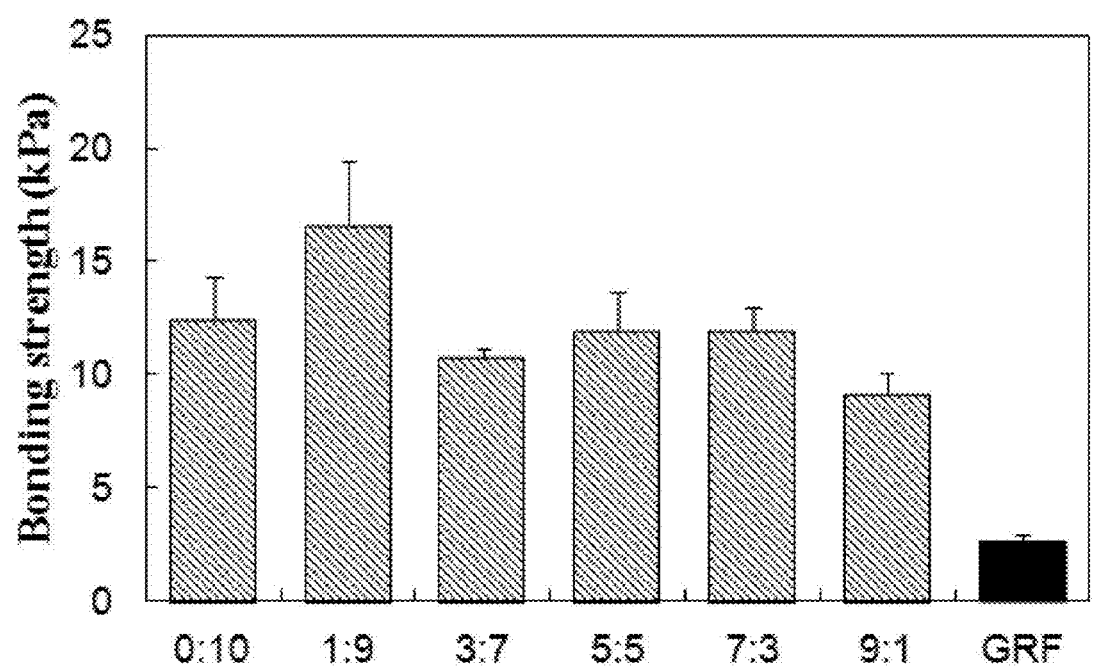

Image of cross-section stained with
hematoxylin and eosin
(Condition: 4Chol-Gltn/Gltn=0:10
40wt% soln.(0.1M PBS pH7.4)
4S-PEG 4.5mM(0.1M PBS pH7.4))

Image of cross-section stained with
hematoxylin and eosin
(Condition: 4Chol-Gltn/Gltn=1:3
40wt% soln.(0.1M PBS pH7.4)
4S-PEG 4.5mM(0.1M PBS pH7.4))

Image of cross-section stained
with hematoxylin and eosin
(Condition: 4Chol-Gltn/Gltn=3:7
40wt% soln.(0.1M PBS pH7.4)
4S-PEG 4.5mM(0.1M PBS pH7.4))

Image of cross-section stained with hematoxylin and eosin
(Condition: 4Chol-Gltn/Gltn=5:5
40wt% soln.(0.1M PBS pH7.4)
4S-PEG 4.5mM(0.1M PBS pH7.4))

Image of cross-section stained with
hematoxylin and eosin
(Condition: 4Chol-Gltn/Gltn=7:3
40wt% soln.(0.1M PBS pH7.4)
4S-PEG 4.5mM(0.1M PBS pH7.4))

Image of cross-section stained with
hematoxylin and eosin
(Condition: 4Chol-Gltn/Gltr=9:1
40wt% soln.(0.1M PBS pH7.4)
4S-PEG 4.5mM(0.1M PBS pH7.4))

TISSUE ADHESIVE AND METHOD FOR PRODUCING SAME

TECHNICAL FIELD

The present invention relates to a tissue adhesive and a method for producing the same.

BACKGROUND ART

A tissue adhesive means a tissue adhesive to close biological tissues (henceforth referred to as tissues), such as blood vessels and skin, in an operation of cardiovascular surgery, etc. With use of this adhesive, it is possible to prevent blood leaking and such risks so as to improve the safety of the operation.

Tissue adhesives include the following three types. The first tissue adhesive is a cyanoacrylate based tissue adhesive, commercial products of which include DERMABOND. This type of tissue adhesive has a problem in that the biocompatibility is low, whereas the bonding strength is high. The second tissue adhesive is a biopolymer-aldehyde based tissue adhesive, commercial products of which include GRF glue. This type of tissue adhesive also has a problem in that the biocompatibility is low, whereas the bonding strength is high. The third tissue adhesive is a fibrin based tissue adhesive, commercial products of which include Bolheal. Conversely, this type of tissue adhesive has a problem in that the bonding strength is low, whereas the biocompatibility is high.

In recent years, it has been elucidated that a tissue adhesive including human serum albumin (henceforth referred to as HSA) and a crosslinking agent has high bonding strength (Non Patent Literature 1).

HSA is a serum protein made from blood and it is a globular protein having a molecular weight of 69,000 and a diameter of about 10 nm. This is a negatively charged acidic protein. In addition, disuccinimidyl tartarate (henceforth referred to as DST) has been used as the crosslinking agent.

However, since any product using a blood is classified into a medicinal product, considerable efforts are required for the approval and clearance. Moreover, once it is approved as a medicinal product, the usage record has to be kept continually for 20 years after the approval. This problematically requires considerable efforts.

For this reason, it has been considered to use gelatin, which is a non-blood preparation, instead of HSA. For example, Patent Literature 1 has disclosed a medical material prepared by crosslinking gelatin with succinimidized poly-L-glutamic acid. Moreover, Patent Literature 2 relates to a tissue adhesive film and has disclosed a tissue adhesive film made from gelatin or collagen. However, they have a problem in that the bonding strength is not enough.

In addition, Patent Literature 3 relating to a tissue adhesive formulation has disclosed a tissue adhesive formulation which includes a mixture of a synthetic and/or cross-linkable material in a particulate form and a particulate material. However, this tissue adhesive formulation also has a problem in that the bonding strength is not enough.

Moreover, there are papers relating to gelatin in which an alkyl group has been introduced on a side chain thereof (Non Patent Literatures 2 and 3). Furthermore, there is a paper including gelatin in which a cholesteryl group has been introduced on a side chain thereof and a tartaric acid crosslinking agent (Non Patent Literature 4).

Use of a hydrophobically modified gelatin in which a hydrophobic group has been introduced into a gelatin having a molecular weight of not less than 10000 and less than 50000 instead of HSA may make it possible to provide a tissue adhesive having high bonding strength and high biocompatibility.

Bonding properties can be improved if the molecular weight of gelatin is increased. However, there is an instance that, when a porcine-derived gelatin was used, the tissue adhesive did not turn to a liquid state and was hardened into a gel state even if the molecular weight of the gelatin was adjusted to about 20000, and so it failed in uniformly being applied to a bonding part when used as a tissue adhesive, and it was difficult to handle in terms of spreadability. In addition, there is an instance of jelling when it was left at rest at normal temperatures.

Moreover, addition of water-insoluble molecules, such as tartaric acid, to a water solvent made it impossible to uniformly disperse these molecules in the water solvent. A tissue adhesive in which such molecules are not dispersed uniformly caused varied bonding properties such as bonding strength and bonding stability.

Meanwhile, since a tissue adhesive composed of polyethylene glycol di-succinimidyl succinate (PEG-(SS)2), which is a water-soluble crosslinking agent, and HSA, has been approved in the U.S.A. under the product name ProGEL, it is highly probable that PEG-based polymers can be used well as a constituent of a tissue adhesive.

CITATION LIST

Patent Literature

Patent Literature 1: JP-A-9-103479
Patent Literature 2: JP-A-2008-284256
Patent Literature t 3: JP-T-2006-523113

Non Patent Literature

Non Patent Literature 1: J. Bioact. Compact. Polym., 24, 546-559 (2009)
Non Patent Literature 2: Colloids Surf. A, 272, 2006, 8-14
Non Patent Literature 3: J. Appl. Polym. Sci., 105, 2007, 3371-3377
Non Patent Literature 4: Colloids Surf. B, 91, 48-56 (2012).

SUMMARY OF INVENTION

Technical Problem

An objective of the present invention is to provide a tissue adhesive having high bonding strength, stable bonding properties, and excellent spreadability, and a method for producing the same.

Solution to Problem

The present inventors found out that in a tissue adhesive composed of an adhesive component composed of an aqueous solution of a hydrophobically modified, fish-derived gelatin and a curative component composed of an aqueous solution of a water-soluble crosslinking reagent and to be applied to a tissue by mixing the adhesive component with the curative component, use of a hydrophobically modified, fish-derived gelatin from a fish-derived gelatin, and a water-soluble crosslinking reagent made it possible to disperse the adhesive component and the curative component uniformly in an aqueous solution when these components were mixed together, thereby successfully preparing a tissue adhesive, and thereby successfully producing a tissue adhesive having stable bonding properties. They found out that this tissue adhesive has high bonding strength and can be applied to a tissue uniformly without being heated and is excellent in spreadability because it was not in a gel state but in a liquid state before curing. Thus, the present invention has been accomplished.

The tissue adhesive of the present invention is characterized by the following.

It is a tissue adhesive to be applied to a tissue by mixing an adhesive component including an aqueous solution of a fish-derived gelatin with a curative component including an aqueous solution of a water-soluble crosslinking reagent, wherein the water-soluble crosslinking reagent has an amide linkage or an ethylene glycol unit or a sugar chain in the molecular main chain thereof and has two or more of an active ester group or an acid anhydride or an aldehyde group.

The fish-derived gelatin of the adhesive component is a hydrophobically modified, fish-derived gelatin having a hydrophobic group on a side chain thereof.

The fish-derived gelatin includes, as its main chain, a fish-derived gelatin in which the number of hydroxyproline per 1000 constitutional amino acids thereof is 90 or less.

The hydrophobically modified, fish-derived gelatin includes Lys and a part of the amino groups of the Lys have been substituted with a hydrophobic group.

The hydrophobic groups include one type or a combination of two or more types selected from the group consisting of an ethyl group (2 carbon atoms), propyl (3 carbon atoms), a butyl group (4 carbon atoms), a pentyl group (5 carbon atoms), a hexanoyl group (6 carbon atoms), a heptanoyl group (7 carbon atoms), an octanoyl group (8 carbon atoms), a nonanoyl group (9 carbon atoms), a decanoyl group (10 carbon atoms), an undecanoyl group (11 carbon atoms), a dodecanoyl group (12 carbon atoms), a tridecanoyl group (13 carbon atoms), a tetradecanoyl group (14 carbon atoms), a pentadecanoyl group (15 carbon atoms), a hexadecanoyl group (16 carbon atoms), a heptadecanoyl group (17 carbon atoms), a stearoyl group (18 carbon atoms), which are saturated fatty acids; isopropyl (3 carbon atoms), an isobutyl group (4 carbon atoms), an isopentyl group (5 carbon atoms), an isohexanoyl group (6 carbon atoms), an isoheptanoyl group (7 carbon atoms), an isooctanoyl group (8 carbon atoms), an isononanoyl group (9 carbon atoms), an isodecanoyl group (10 carbon atoms), an isoundecanoyl group (11 carbon atoms), an isododecanoyl group (12 carbon atoms), an isotridecanoyl group (13 carbon atoms), an isotetradecanoyl group (14 carbon atoms), an isopentadecanoyl group (15 carbon atoms), an isohexadecanoyl group (16 carbon atoms), an isopalmityl group (16 carbon atoms), an isoheptadecanoyl group (17 carbon atoms), an isostearoyl group (18 carbon atoms), which are branched saturated fatty acids; an oleyl group (18 carbon atoms, one unsaturated carbon atom), a linolenyl group (18 carbon atoms, two unsaturated carbon atoms), an α-linolenyl group (18 carbon atoms, three unsaturated carbon atoms), which are unsaturated fatty acids; and a cholesteryl group, which is a cell membrane component.

The fish-derived gelatin is a fish-derived gelatin derived from tilapia, sea bream, or cod.

The molecular weight of the hydrophobically modified, fish-derived gelatin is not less than 50000 and less than 100000.

The water-soluble crosslinking reagent includes one type or a combination of two or more types selected from the group consisting of polyethylene glycol di-succinimidyl succinate, pentaerythritol poly(ethylene glycol) ether tetra-succinimidyl glutarate, succinimidized poly-L-glutamic acid, an aldehyde group-introduced starch, and an aldehyde group-introduced dextran.

The water solvent used for the aqueous solution of the fish-derived gelatin and the water solvent used for the aqueous solution of the water-soluble crosslinking reagent are each a phosphate buffer solution (PBS) having a pH of from 6.0 to 8.0.

A fish-derived hydrophobically unmodified, gelatin is further contained as the adhesive component.

The aqueous solution of the hydrophobically modified, fish-derived gelatin is liquid at normal temperatures.

The method for producing the tissue adhesive of the present invention is characterized by the following.

There are included:

a step of synthesizing a hydrophobically modified, fish-derived gelatin by adding an organic molecule having a hydrophobic group to a solution comprising the fish-derived gelatin in the presence of amine to substitute a part of the amino groups on a side chain of the fish-derived gelatin, wherein the fish-derived gelatin has the number of hydroxyproline per 1000 constitutional amino acids is 90 or less, a step of preparing an adhesive component comprising an aqueous solution of the hydrophobically modified, fish-derived gelatin by dispersing the hydrophobically modified, fish-derived gelatin in a phosphate buffer solution, and a step of preparing a curative component comprising an aqueous solution of a water-soluble crosslinking reagent by dispersing the water-soluble crosslinking reagent in a phosphate buffer solution, wherein the water-soluble crosslinking reagent has the molecular main chain of which comprises an amide linkage or an ethylene glycol unit or a sugar chain and two or more of an active ester group or an acid anhydride or an aldehyde group.

The step of preparing the adhesive component includes a step of mixing the aqueous solution of the hydrophobically modified, fish-derived gelatin with the aqueous solution of the fish-derived gelatin prepared by dispersing the fish-derived gelatin in the phosphate buffer solution.

The aqueous solution of the hydrophobically modified, fish-derived gelatin and the aqueous solution of the fish-derived gelatin are mixed in a weight ratio of not less than 1:9 and less than 5:5.

There is included a step of mixing:

an adhesive component including an aqueous solution of a fish-derived gelatin, and a curative component including an aqueous solution of a water-soluble crosslinking reagent, wherein the molecular main chain of the water-soluble molecule includes an amide linkage or an ethylene glycol unit or a sugar chain and also has two or more of an active ester group or an acid anhydride or an aldehyde group.

Advantageous Effects of Invention

The tissue adhesive of the present invention can be prepared by dispersing the hydrophobically modified, fish-derived gelatin and the water-soluble crosslinking reagent uniformly in an aqueous solution and thereby a tissue adhesive having stable bonding properties can be produced. In addition, it is possible to make a tissue adhesive that is not in a gel state but can be in a liquid state and that can be applied to a tissue uniformly and is excellent in spreadability. Covalent bond can be formed by increasing a molecular weight and crosslinking the amino groups of the hydrophobically modified, gelatin molecules with an active ester group or an acid anhydride or an aldehyde group of the crosslinking reagent. Furthermore, bonding strength can be enhanced and the hydrophobically modified, gelatin can be decomposed readily by an enzyme (collagenase) in the course of wound healing and biocompatibility can be enhanced by anchoring the hydrophobic groups into a tissue and thereby forming physically firm bond.

Since the method for producing the tissue adhesive of the present invention is configured to include a step of adding an organic molecule having a hydrophobic group to a solution in which a fish-derived gelatin in which the number of hydroxyproline per 1000 constitutional amino acids is 90 or less is dissolved to substitute a part of the amino groups on a side chain of the fish-derived gelatin, thereby synthesizing a hydrophobically modified, fish-derived gelatin, a step of dispersing the hydrophobically modified, fish-derived gelatin in a phosphate buffer solution, thereby preparing an adhesive component composed of an aqueous solution containing the hydrophobically modified, fish-derived gelatin, and a step of dispersing a water-soluble crosslinking reagent, the molecular main chain of which includes an amide linkage or an ethylene glycol unit or a sugar chain and which has two or more of an active ester group or an acid anhydride or an aldehyde group, in a phosphate buffer solution, thereby preparing a curative component composed of an aqueous solution containing the water-soluble crosslinking reagent, it is possible to prepare a tissue adhesive by dispersing the hydrophobically modified, fish-derived gelatin and the water-soluble crosslinking reagent uniformly in an aqueous solution and easily prepare a tissue adhesive being high in bonding strength, stable in bonding properties, and excellent in spreadability.

The method for producing a tissue adhesive of the present invention preferably includes the step of mixing the aqueous solution of the hydrophobically modified, fish-derived gelatin with the aqueous solution of the fish-derived gelatin prepared by dispersing the fish-derived gelatin in the phosphate buffer solution, and by so doing, it is possible to prepare a tissue adhesive by dispersing hydrophobically modified, the fish-derived gelatin and the water-soluble crosslinking reagent uniformly in an aqueous solution and easily prepare a tissue adhesive being high in bonding strength, stable in bonding properties, and excellent in spreadability. In addition, aggregation of hydrophobic groups can be inhibited and the bonding strength of a tissue adhesive can be improved.

BRIEF DESCRIPTION OF DRAWINGS

FIG. 1 is a schematic diagram illustrating an example of the tissue adhesive of the present invention.

FIG. 11 is a cross-sectional image of a tissue stained with hematoxylin and eosin after a bonding strength measurement using the adhesive of Test Example 2-3.
The conditions for the preparation of the adhesive of Test Example 2-3 include Gltn 40 wt % soln. 4S-PEG 4.5 mM (0.1 M PBS pH 7.0).

FIG. 16 is a graph of the dependency of bonding strength on the weight ratio of a 4Chol-Gltn solution to a Gltn solution.

The conditions for the preparation of the adhesive of Example 3-5 include 4Chol-Gltn/Gltn=7:3 40 wt % soln. (0.1M PBS pH 7.4), and 4S-PEG 4.5 mM (0.1M PBS pH 7.4).

Figure 22:
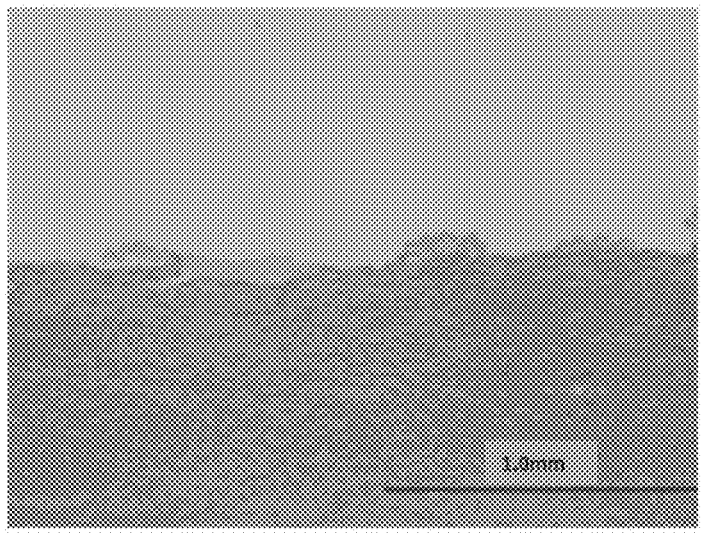

FIG. 22 is a cross-sectional image of a tissue stained with hematoxylin and eosin after a bonding strength measurement using the adhesive of Example 3-6.
The conditions for the preparation of the adhesive of Example 3-6 include 4Chol-Gltn/Gltn=9:1 40 wt % soln. (0.1M PBS pH 7.4), and 4S-PEG 4.5 mM (0.1M PBS pH 7.4).

Figure 23:
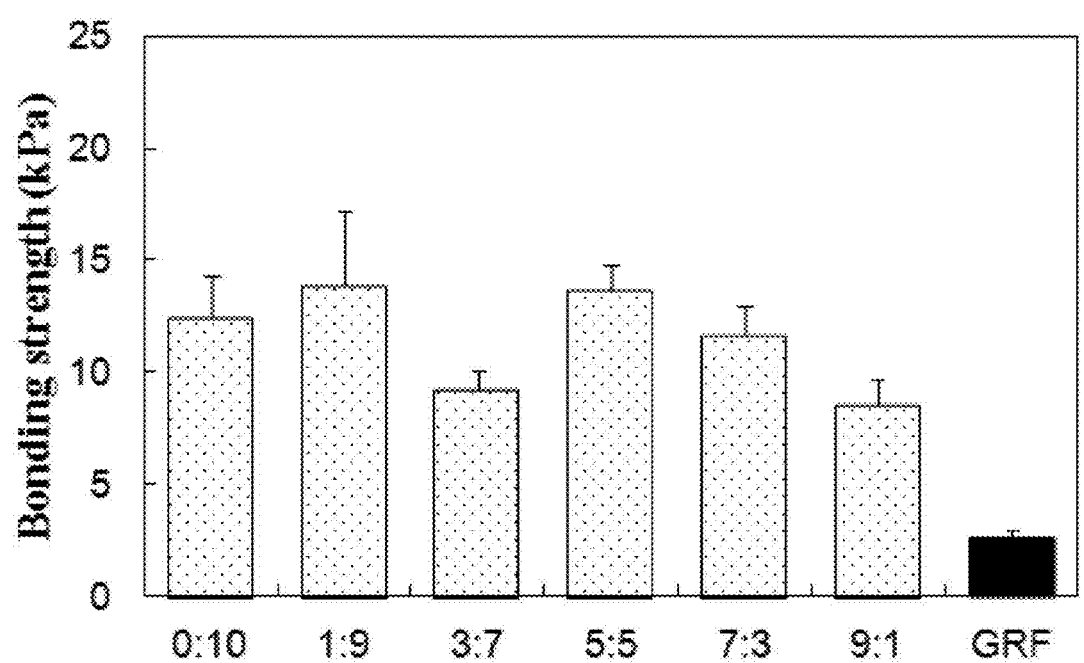

FIG. 23 is a graph of the dependency of bonding strength on the weight ratio of a 7Chol-Gltn solution to a Gltn solution.

Figure 24:
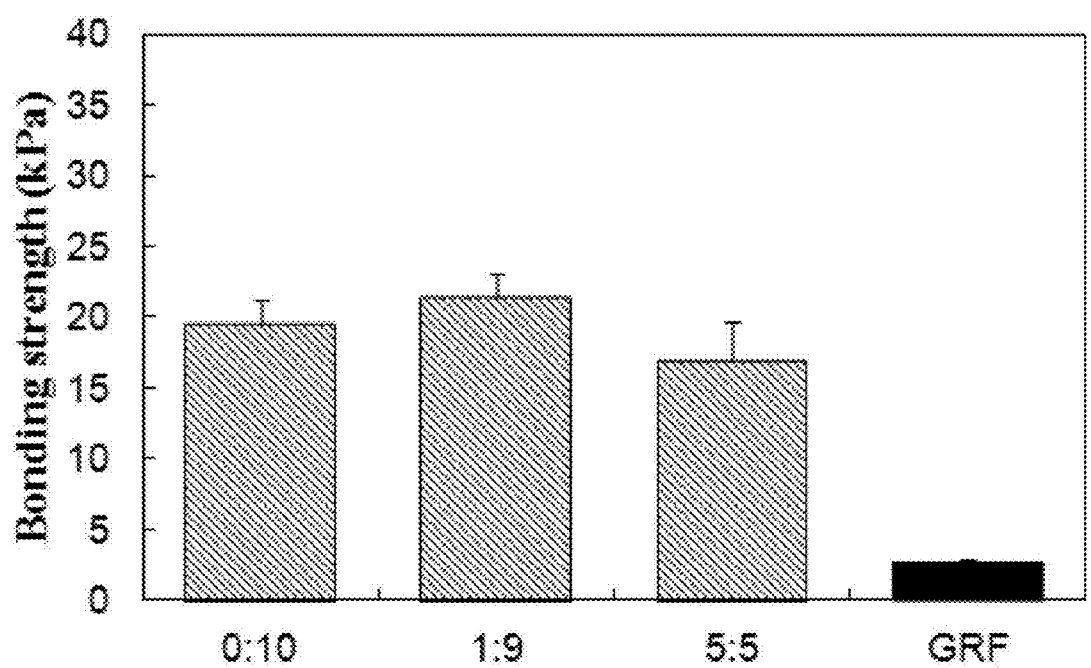

FIG. 24 is a graph of the dependency of bonding strength on the weight ratio of a 4Chol-Gltn solution to a Gltn solution.

Figure 25:
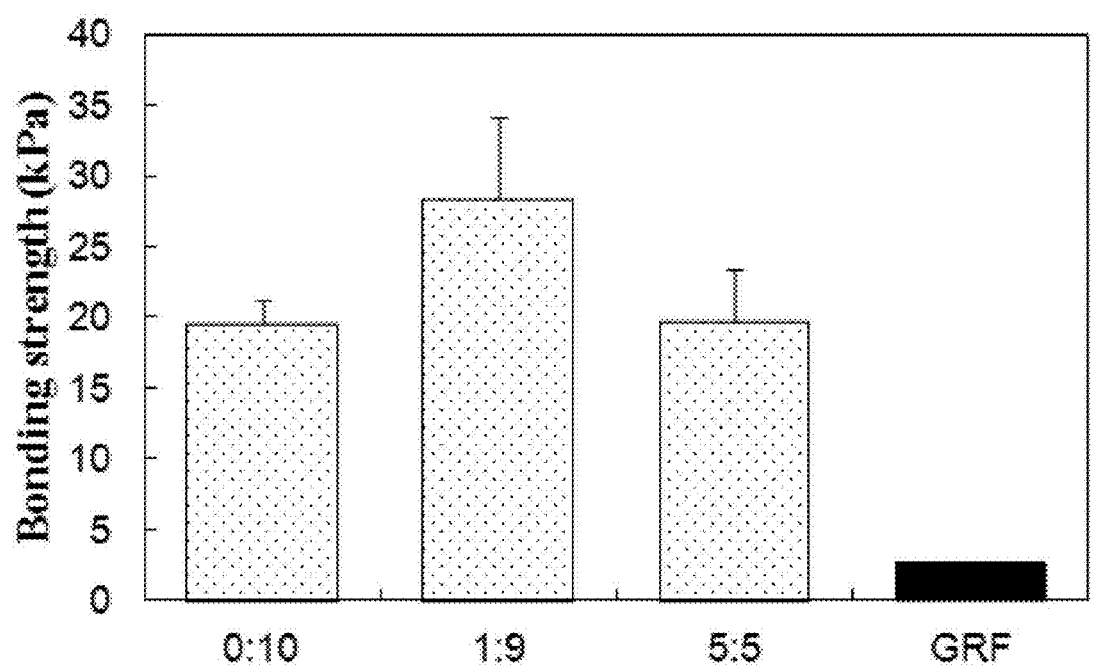

FIG. 25 is a graph of the dependency of bonding strength on the weight ratio of a 7Chol-Gltn solution to a Gltn solution.

Figure 26:
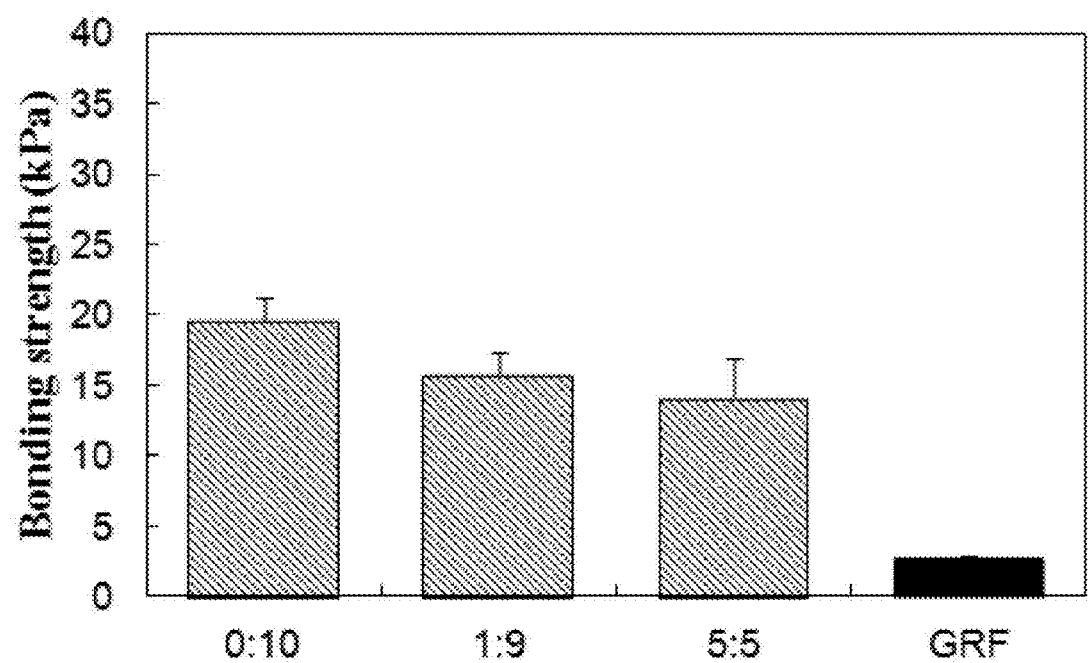

FIG. 26 is a graph of the dependency of bonding strength on the weight ratio of a 23Chol-Gltn solution to a Gltn solution.

Figure 27:
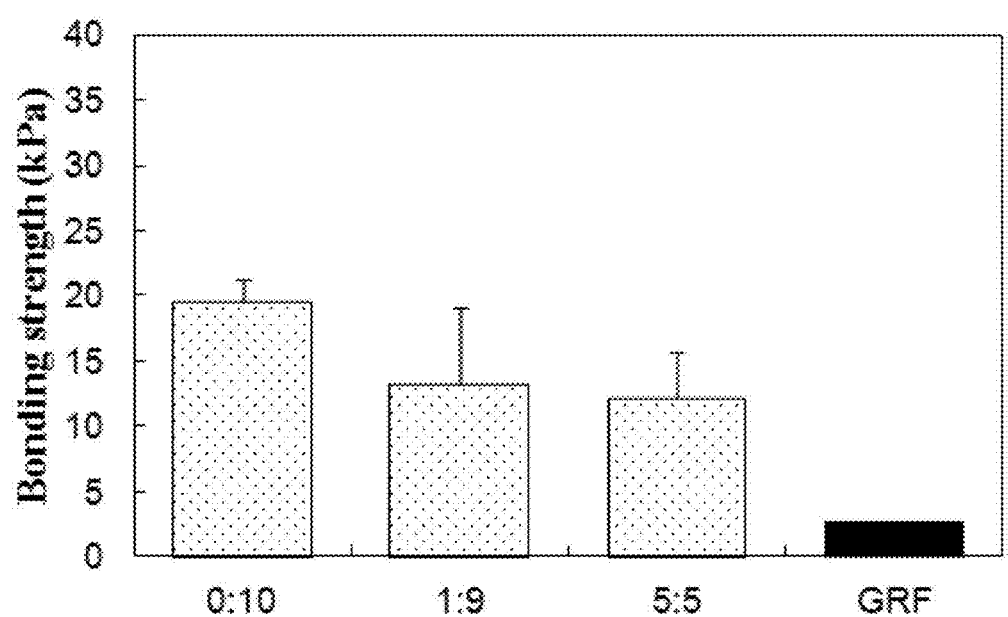

FIG. 27 is a graph of the dependency of bonding strength on the weight ratio of a 70Chol-Gltn solution to a Gltn solution.

Figure 28:
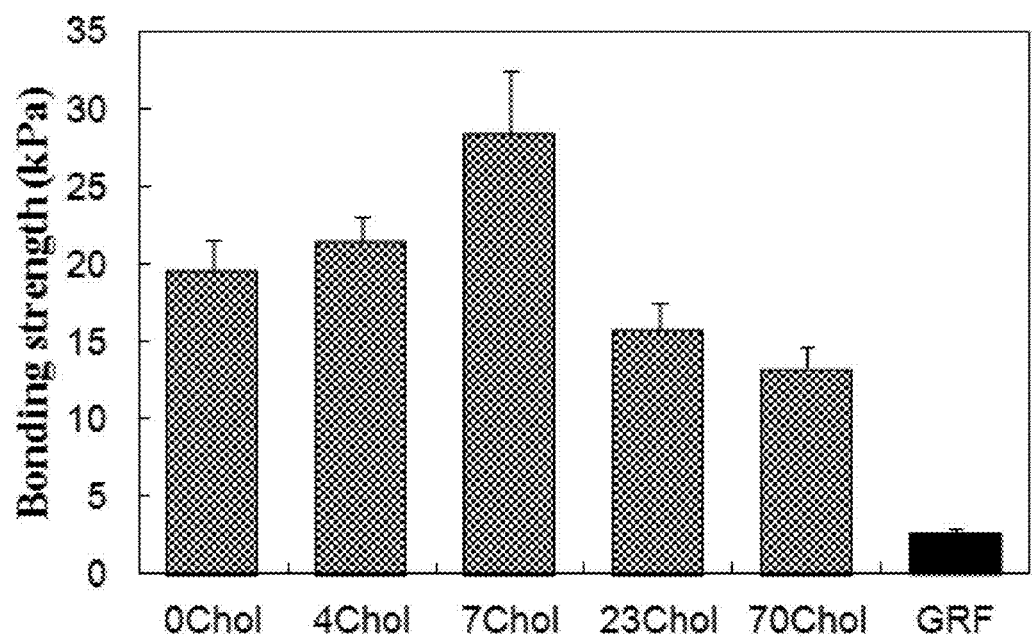

FIG. 28 is a graph showing the dependency of the bonding strength of a tissue adhesive in a weight ratio of 1:9 on the hydrophobic group introduction ratio.

Figure 29:
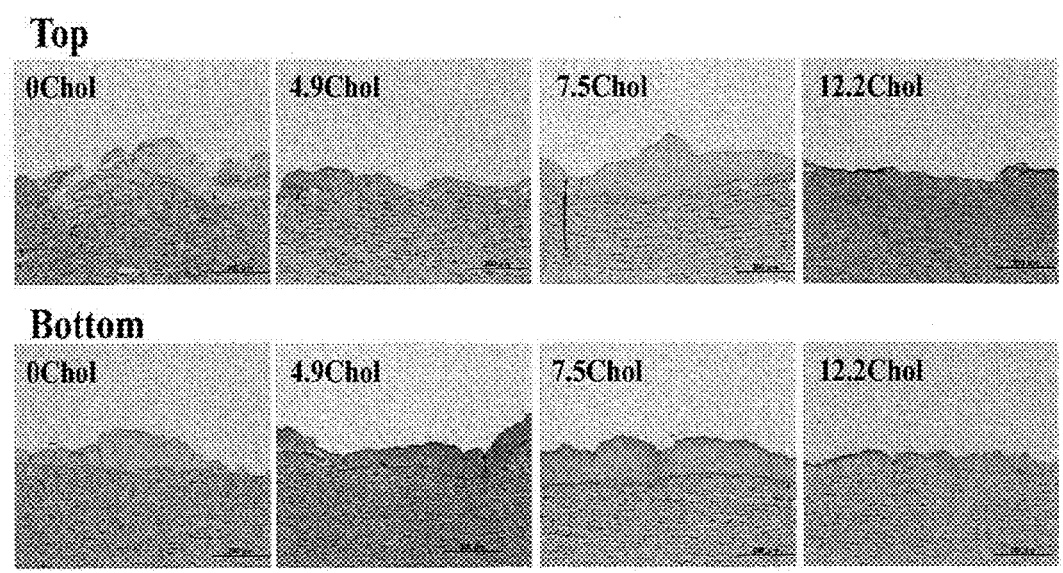

FIG. 29 includes microphotographs each showing the condition of a fracture surface of a porcine aortic media in the cases where a hydrophobically modified, cod gelatin having a hydrophobic group introduction ratio by cholesteryl group of 4.9 mol %, 7.5 mol %, or 12.2 mol % was used as an adhesive component.

DESCRIPTION OF EMBODIMENTS

Embodiments of the Present Invention

Hereunder is a description of a tissue adhesive and a method for producing the same, which are the embodiments of the present invention, with reference to the appended drawings.

The tissue adhesive serving as an embodiment of the present invention is a tissue adhesive to be applied to a tissue by mixing an adhesive component including an aqueous solution of a fish-derived gelatin with a curative component including an aqueous solution of a water-soluble crosslinking reagent. Especially, it is preferred to use a hydrophobically modified, fish-derived gelatin having a hydrophobic group on a side chain thereof as the fish-derived gelatin.

In FIG. 1 is illustrated an embodiment having a hydrophobically modified, fish-derived gelatin and a water-soluble crosslinking reagent.

The hydrophobically modified, fish-derived gelatin is a macromolecule in which two or more amino acids are connected linearly. A part of the amino groups of Lys contained as the amino acid have been substituted with the aforementioned hydrophobic groups. Lys is one of the protein-constituting α-amino acids and it is an essential amino acid. It is an amino acid having an ε-amino group on the side chain.

A part of the amino groups of Lys can be easily substituted with a hydrophobic group and a part of the amino groups of Lys of the hydrophobically modified, fish-derived gelatin have been substituted with a hydrophobic group.

Preferably, the hydrophobically modified, fish-derived gelatin contains, as its main chain, a fish-derived gelatin in which the number of hydroxyproline represented by the following formula (1) per 1000 constitutional amino acids thereof is 90 or less and has an amino group and a hydrophobic group on a side chain thereof.

[Chemical Formula 1]

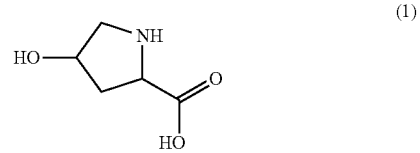

By the use of a fish-derived gelatin skeleton, the adhesive can be readily decomposed by an enzyme and therefore the biocompatibility can be enhanced. Moreover, dispersability in a water solvent can be enhanced.

Preferably, the fish-derived gelatin is a gelatin derived from fish of tilapia, sea bream, or cod. This makes it possible to prepare a tissue adhesive by dispersing the fish-derived gelatin uniformly in an aqueous solution and to make a tissue adhesive that is not in a gel state but can be in a liquid state and that can be applied to a tissue uniformly and is excellent in spreadability.

The molecular weight of the hydrophobically modified, fish-derived gelatin is preferably not less than 50000 and less than 100000. By adjusting the molecular weight to 50000 or more, bonding strength can be increased. Since the hydrophobically modified, fish-derived gelatin contains a fish gelatin as its main skeleton, its dispersability in a water solvent is high and it does not gelate and it can be kept in a liquid form even if its molecular weight is adjusted to 50000 or more.

The hydrophobic groups introduced in the fish-derived gelatin anchor to a tissue to fix the fish-derived gelatin firmly to the tissue.
By so doing, the hydrophobically modified, gelatin can be physically firmly bonded to a tissue, and thereby bonding strength can be enhanced.

Examples of such a hydrophobic group include a cholesteryl group represented by the following formula (2).

[Chemical Formula 2]

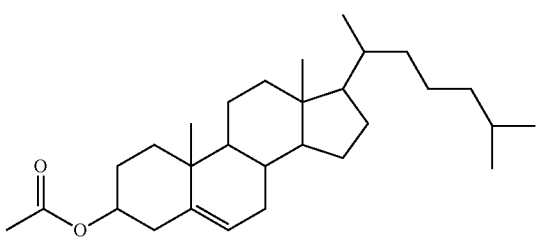

The hydrophobic groups may include one type or a combination of two or more types of an ethyl group (2 carbon atoms), propyl (3 carbon atoms), a butyl group (4 carbon atoms), a pentyl group (5 carbon atoms), a hexanoyl group (6 carbon atoms), a heptanoyl group (7 carbon atoms), an octanoyl group (8 carbon atoms), a nonanoyl group (9 carbon atoms), a decanoyl group (10 carbon atoms), an undecanoyl group (11 carbon atoms), a dodecanoyl group (12 carbon atoms), a tridecanoyl group (13 carbon atoms), a tetradecanoyl group (14 carbon atoms), a pentadecanoyl group (15 carbon atoms), a hexadecanoyl group (16 carbon atoms), a heptadecanoyl group (17 carbon atoms), a stearoyl group (18 carbon atoms), which are saturated fatty acids; isopropyl (3 carbon atoms), an isobutyl group (4 carbon atoms), an isopentyl group (5 carbon atoms), an isohexanoyl group (6 carbon atoms), an isoheptanoyl group (7 carbon atoms), an isooctanoyl group (8 carbon atoms), an isononanoyl group (9 carbon atoms), an isodecanoyl group (10 carbon atoms), an isoundecanoyl group (11 carbon atoms), an isododecanoyl group (12 carbon atoms), an isotridecanoyl group (13 carbon atoms), an isotetradecanoyl group (14 carbon atoms), an isopentadecanoyl group (15 carbon atoms), an isohexadecanoyl group (16 carbon idyl or N-hydroxysulfosuccinimidyl groups. This is because succinimide is a succinic acid derivative existing in a metabolic pathway in vivo, and has been actually used for an FDA sanctioned tissue adhesive (sealant).

The water-soluble crosslinking reagent may include one type or a combination of two or more types selected from the group consisting of 4S-PEG, PEG-(SS)2, succinimidized poly-L-glutamic acid, an aldehyde group-introduced starch, and an aldehyde group-introduced dextran.

Examples of the water-soluble crosslinking reagent include pentaerythritol poly(ethylene glycol) ether tetrasuccinimidyl glutarate (abbreviated as 4S-PEG) represented by the following formula (3).

Preferably, n is not greater than 60.

Preferably, the molecular weight is adjusted to about 10,000.

[Chemical Formula 3]

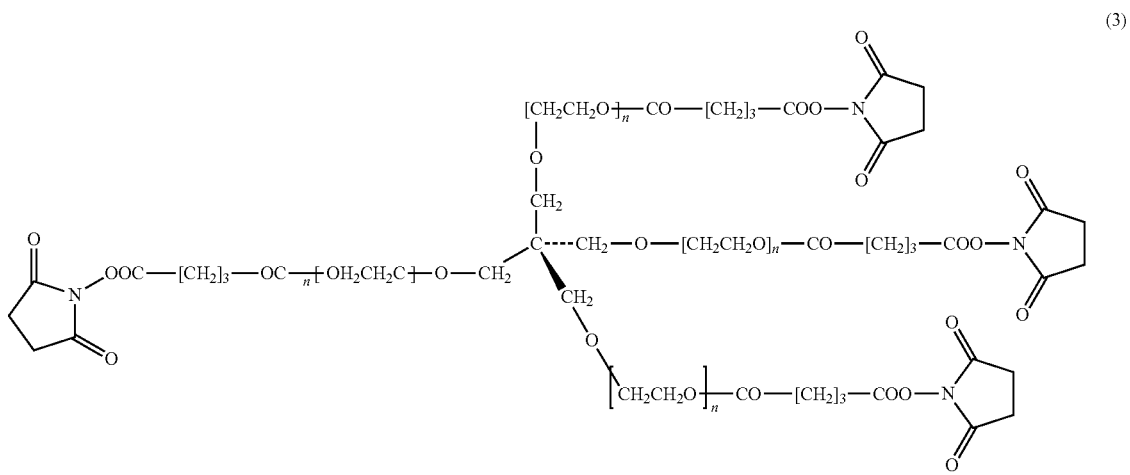

(3)

atoms), an isopalmityl group (16 carbon atoms), an isoheptadecanoyl group (17 carbon atoms), an isostearoyl group (18 carbon atoms), which are branched saturated fatty acids; an oleyl group (18 carbon atoms, one unsaturated carbon atom), a linolenyl group (18 carbon atoms, two unsaturated carbon atoms), an α-linolenyl group (18 carbon atoms, three unsaturated carbon atoms), which are unsaturated fatty acids; and a cholesteryl group, which is a cell membrane component. This makes it possible to enhance bonding strength by anchoring hydrophobic groups into a tissue and thereby forming physically firm bond.

The water-soluble crosslinking reagent has an amide linkage, an ethylene glycol unit or a sugar chain on the molecule main chain thereof and also has two or more of an active ester group, an acid anhydride, or an aldehyde group.

Since the molecule main chain of the water-soluble crosslinking reagent has an amide linkage, an ethylene glycol unit, or a sugar chain, the water-soluble crosslinking reagent exhibits high water solubility, so that an increased dispersability can be exhibited in a water solvent. By having two or more of an active ester group, an acid anhydride, or an aldehyde group in one molecule, the water-soluble crosslinking reagent can react and bond with two amino groups of a hydrophobically modified, fish-derived gelatin and it can form a firm bond structure by crosslinking two or more fish-derived gelatins.

The active ester group is preferably any one type or a combination of two or more types of N-hydroxysuccinim- A phosphate buffer solution may be used as the water solvent. The pH value is preferably adjusted to 5 to 9, more preferably 6 to 8. Thereby, it is possible to make a hydrophobically modified, fish-derived gelatin and a water-soluble crosslinking reagent efficiently undergo a crosslinking reaction via a water solvent when bonding a body tissue.

<Bonding of Tissue by Use of Tissue Adhesive of this Embodiment>

Next, a description is made to bonding of tissue by use of the tissue adhesive of this embodiment.

First, two pieces of tissue each being approximately rectangular in plan (for example, 1 cm in length, 1 cm in width, and 0.5 cm in height) are prepared. Regarding the tissue, a collagen casing composed of collagen, cellulose, glycerin, and other components can be used as an imitation skin.

Then, after applying a liquid adhesive component and a liquid curative component to one surface of one tissue by using a double-syringe injector, these components are mixed on that surface.

Next, after pushing the other tissue so that that part coated with the adhesive may be covered, a weight is put on the opposite surface and the set is left at rest under loading weight for a prescribed period of time.

The leaving time is necessary for the tissue adhesive to be solidified, and is appropriately set according to the proportion of the constituent materials in the tissue adhesive.

Preferably, it is limited to about 10 minutes at most. In this case, it is preferred to heat and perform incubation at a temperature of 37° C. or less, for example. By so doing, the curing rate can be increased. The set may be left stand at room temperature after the bonding and until it solidifies.

Preferably, the tissue adhesive is applied after being pre-incubated at a temperature of 37° C. or less before use.

Figure 2:
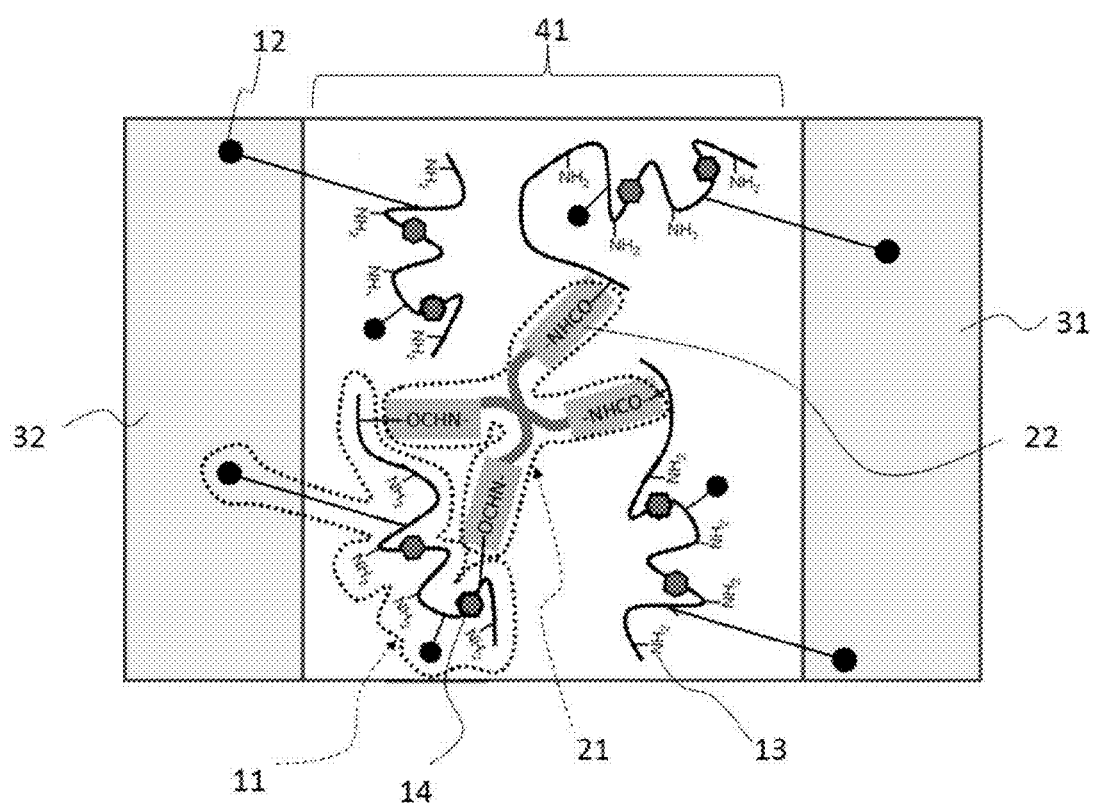
FIG. 2 is a schematic diagram illustrating an example of adhesion by use of the tissue adhesive of the present invention.
Figure 3:
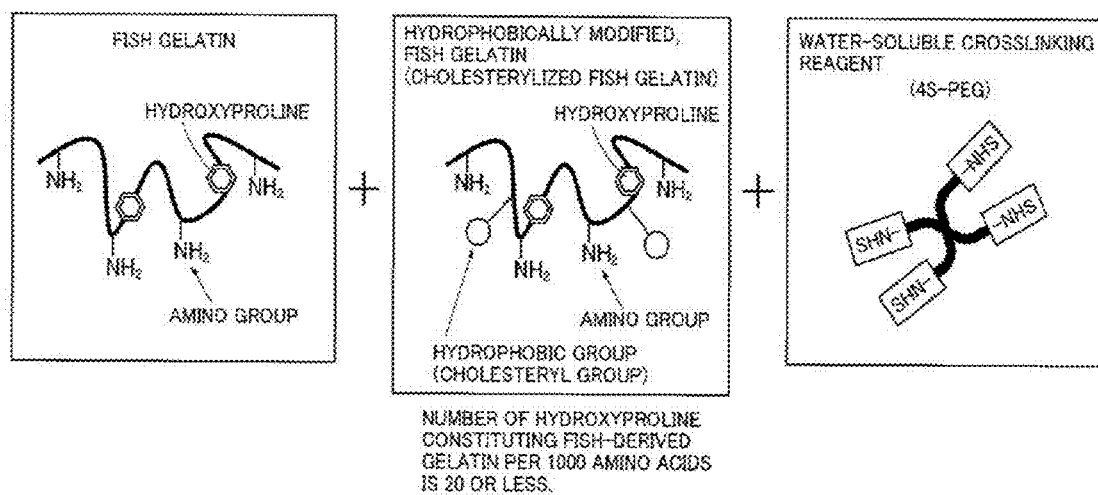
FIG. 3 is a schematic diagram illustrating an example of the tissue adhesive of the present invention.

FIG. 2 is a schematic diagram illustrating an example of tissue bonding by use of the tissue adhesive serving as an embodiment of the present invention.

An amino group of the hydrophobically modified, fish-derived gelatin reacts with an active ester group of the crosslinking reagent in a hydrolysis reaction represented by the following formula (4), and thereby an amide linkage is formed. At this time, N-hydroxysuccinimide in the active ester group is separated. In the formula (4), —COOR represents an active ester of the water-soluble crosslinking reagent and —NH$_2$ represents an amino group of the hydrophobically modified, fish-derived gelatin.

【化4】

[Chemical Formula 4]

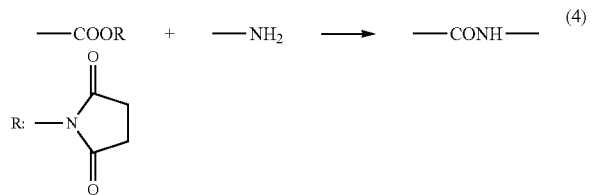

(4)

By execution of this crosslinking reaction in a chain-like manner, a structure in which a plurality of molecules of the hydrophobically modified, fish-derived gelatin is chemically firmly bonded by the water-soluble crosslinking reagent is formed.

The active ester group of this water-soluble crosslinking reagent is also capable of reacting with amino groups of a hydrophobically modified, fish-derived gelatin and proteins, such as collagen, existing in a biological tissue to form an amide linkage. By so doing, a structural that is more chemically firmly bonded is formed.

As shown in FIG. 2, hydrophobic groups each having a certain molecular weight and size permeates a tissue by a hydrophobic interaction, so that the hydrophobically modified, fish-derived gelatin is firmly fixed to the tissue. By so doing, the construct is physically firmly bonded to the surface of the tissue.

More preferably, the adhesive component includes a hydrophobically modified, fish-derived gelatin and an hydrophobically unmodified, fish-derived gelatin. By this, aggregation of hydrophobic groups can be inhibited and the bonding strength of the tissue adhesive can thereby be enhanced.

<Method for Producing Tissue Adhesive>

Next, a description is made to a method for producing a tissue adhesive serving as an embodiment of the present invention.

The method for producing of the tissue adhesive serving as an embodiment of the present invention includes a step of mixing an adhesive component including an aqueous solution of a fish-derived gelatin with a curative component including an aqueous solution of a water-soluble crosslinking reagent, wherein the molecular main chain of the water-soluble molecule includes an amide linkage or an ethylene glycol unit or a sugar chain and also has two or more of an active ester group or an acid anhydride or an aldehyde group.

The method for producing a tissue adhesive of the present invention more preferably includes a hydrophobically modified, fish-derived gelatin synthesis step S1, an adhesive component preparation step S2, and a curative component preparation step S3.

(Hydrophobically Modified, Fish-Derived Gelatin Synthesis Step S1)

First, a hydrophobically modified, fish-derived gelatin is synthesized by adding an organic molecule having a hydrophobic group to a solution in which a fish-derived gelatin in which the number of hydroxyproline per 1000 constitutional amino acids is 90 or less is dissolved in the presence of an amine to substitute a part of the amino groups on a side chain of the fish-derived gelatin.

For example, an acid chloride having a hydrophobic group reactive with an amino group is mixed with a fish-derived gelatin dissolved in an organic solvent in the presence of triethylamine, preparing a mixed solution in a container.

As the organic solvent, dimethylsulfoxide (DMSO) can be used, for example.

The organic molecule may be exemplified by cholesteryl chloroformate represented by the following formula (5).

Next, the mixture solution is heated and stirred under an inert gas atmosphere. For example, this can be done under a nitrogen atmosphere at a heating temperature of 80° C. for a stirring time of a day and a night.

[Chemical Formula 5]

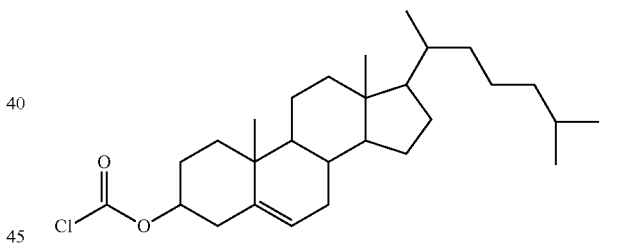

(5)

Next, this mixed solution is added dropwise to an ice cold ethanol solvent. Next, this solution is filtrated through a glass filter or the like.

Furthermore, the filtrated matter is washed with an organic solvent. By so doing, impurities in the filtrated matter can be removed so as to increase the purity of the hydrophobically modified, fish-derived gelatin. Regarding this organic solvent for the washing purpose, ethanol or ethyl acetate can be used, for example.

By the above-mentioned step, a hydrophobically modified, fish-derived gelatin in which a part of the amino groups on side chains of a fish-derived gelatin have been substituted with a hydrophobic group can be produced.

(Adhesive Component Preparation Step S2)

The hydrophobically modified, fish-derived gelatin is dispersed in a phosphate buffer solution, thereby preparing an adhesive component composed of an aqueous solution containing the hydrophobically modified, fish-derived gelatin.

The time before the solidification can be appropriately set by appropriately setting the pH of the phosphate buffer solution. A crosslinking reaction at the time of mixing can be advanced rapidly by use of the buffer solution having a pH of 6 to 8.

(Curative Component Preparation Step S3)

A water-soluble crosslinking reagent, the molecular main chain of which includes an amide linkage or an ethylene glycol unit or a sugar chain and which has two or more of an active ester group or an acid anhydride or an aldehyde group, is dispersed in a phosphate buffer solution and thereby a curative component composed of an aqueous solution containing the water-soluble crosslinking reagent is prepared.

The time before the solidification can be appropriately set by appropriately setting the pH of the phosphate buffer solution. A crosslinking reaction at the time of mixing can be advanced rapidly by use of the buffer solution having a pH of 6 to 8.

By executing the steps described above, the tissue adhesive serving as an embodiment of the present invention can be produced easily.

By mixing the adhesive component with the curative component, applying the mixture to a tissue, and then adhering another tissue, the two tissues can easily be bonded together.

<Method for Producing Tissue Adhesive (Another Example)>

Next, a description is made to another example of the method for producing a tissue adhesive serving as an embodiment of the present invention.

The other example of the method for producing a tissue adhesive serving as an embodiment of the present invention includes a hydrophobically modified, fish-derived gelatin synthesis step S11, a step S12 of preparing an aqueous solution containing a hydrophobically modified, fish-derived gelatin, a step S13 of preparing an aqueous solution containing a fish-derived gelatin, an adhesive component preparation step S14, and a curativecurative component preparation step S15.

The hydrophobically modified, fish-derived gelatin synthesis step 511 is the same step as the hydrophobically modified, fish-derived gelatin synthesis step S1 descried previously.

The step S12 of preparing an aqueous solution containing a hydrophobically modified, fish-derived gelatin is the same as the adhesive component preparation step S2 described previously.

(Step S13 of Preparing an Aqueous Solution Containing a Fish-Derived Gelatin)

By dispersing a fish-derived gelatin in a phosphate buffer solution, an aqueous solution containing the fish-derived gelatin is prepared.

The time before the solidification can be appropriately set by appropriately setting the pH of the phosphate buffer solution. A crosslinking reaction at the time of mixing can be advanced rapidly by use of the buffer solution having a pH of 6 to 8.

(Adhesive Component Preparation Step S14)

An adhesive component composed of a mixed solution is prepared by mixing the aqueous solution containing the hydrophobically modified, fish-derived gelatin with the aqueous solution containing the fish-derived gelatin. The weight ratio is preferably adjusted to 1:9 to 5:5, more preferably 1:9. By so doing, the dispersability can be improved and aggregation can be inhibited.

The curative component preparation step S15 is the same step as the curative component preparation step S3 described previously.

By executing the steps described above, the tissue adhesive serving as an embodiment of the present invention can be produced easily.

By mixing the adhesive component with the curative component, applying the mixture to a tissue, and then adhering another tissue, the two tissues can easily be bonded together.

Preferably, the volume ratio of the adhesive component to the curative component is adjusted to about 1:1. The dispersability can thereby be improved.

The tissue adhesive serving as an embodiment of the present invention can be prepared by dispersing the hydrophobically modified, fish-derived gelatin and the water-soluble crosslinking reagent uniformly in an aqueous solution and thereby a tissue adhesive having stable bonding properties can be produced. In addition, it is possible to make a tissue adhesive that is not in a gel state but can be in a liquid state and that can be applied to a tissue uniformly and is excellent in spreadability. In addition, covalent bond can be formed by making larger a molecular weight and crosslinking the amino groups of the hydrophobically modified, gelatin molecules with the active ester group or the acid anhydride or the aldehyde group of the crosslinking reagent. Furthermore, bonding strength can be enhanced and the hydrophobically modified, gelatin can be decomposed readily by an enzyme (collagenase) in the course of wound healing and biocompatibility can be enhanced by anchoring the hydrophobic groups into a tissue and thereby forming physically firm bond.

Since the tissue adhesive serving as an embodiment of the present invention is configured such that the hydrophobically modified, fish-derived gelatin is a polymer in which two or more amino acids are linearly linked and a part of the amino groups of Lys contained as the amino acids are substituted with a hydrophobic group, covalent bond can be formed by crosslinking the amino groups existing in the fish-derived gelatin by the active ester groups of the crosslinking reagent and thereby the bonding strength can be improved, and the hydrophobically modified, gelatin can readily be decomposed by an enzyme (collagenase) in the course of wound healing and the biocompatibility can thereby be enhanced.

The tissue adhesive serving as an embodiment of the present invention is configured such that the hydrophobic groups include one type or a combination of two or more types selected from the group consisting of an ethyl group (2 carbon atoms), propyl (3 carbon atoms), a butyl group (4 carbon atoms), a pentyl group (5 carbon atoms), a hexanoyl group (6 carbon atoms), a heptanoyl group (7 carbon atoms), an octanoyl group (8 carbon atoms), a nonanoyl group (9 carbon atoms), a decanoyl group (10 carbon atoms), an undecanoyl group (11 carbon atoms), a dodecanoyl group (12 carbon atoms), a tridecanoyl group (13 carbon atoms), a tetradecanoyl group (14 carbon atoms), a pentadecanoyl group (15 carbon atoms), a hexadecanoyl group (16 carbon atoms), a heptadecanoyl group (17 carbon atoms), a stearoyl group (18 carbon atoms), which are saturated fatty acids; isopropyl (3 carbon atoms), an isobutyl group (4 carbon atoms), an isopentyl group (5 carbon atoms), an isohexanoyl group (6 carbon atoms), an isoheptanoyl group (7 carbon atoms), an isooctanoyl group (8 carbon atoms), an isononanoyl group (9 carbon atoms), an isodecanoyl group (10 carbon atoms), an isoundecanoyl group (11 carbon atoms), an isododecanoyl group (12 carbon atoms), an isotridecanoyl group (13 carbon atoms), an isotetradecanoyl group (14 carbon atoms), an isopentadecanoyl group (15 carbon atoms), an isohexadecanoyl group (16 carbon atoms), an isopalmityl group (16 carbon atoms), an isoheptadecanoyl group (17 carbon atoms), an isostearoyl group (18 carbon atoms), which are branched saturated fatty acids; an oleyl group (18 carbon atoms, one unsaturated carbon atom), a linolenyl group (18 carbon atoms, two unsaturated carbon atoms), an α-linolenyl group (18 carbon atoms, three unsaturated carbon atoms), which are unsaturated fatty acids; and a cholesteryl group, which is a cell membrane component, physically firm bond is formed by anchoring hydrophobic groups into a tissue, and thereby bonding strength can be enhanced.

Since the tissue adhesive serving as an embodiment of the present invention is configured such that the fish-derived gelatin is a gelatin derived from a fish among tilapia, sea bream, and cod, the tissue adhesive can be prepared by dispersing the fish-derived gelatin uniformly in an aqueous solution and thereby a tissue adhesive having stable bonding properties can be produced. In addition, it is possible to make a tissue adhesive that is not in a gel state but can be in a liquid state and that can be applied to a tissue uniformly and is excellent in spreadability.

Since the tissue adhesive serving as an embodiment of the present invention is configured such that the molecular weight of the hydrophobically modified, fish-derived gelatin is not less than 50000 and less than 100000, it is possible to make the bond of the tissue adhesive be a covalent bond.

Since the tissue adhesive serving as an embodiment of the present invention is configured such that the water-soluble crosslinking reagent includes one type or a combination of two or more types selected from the group consisting of polyethylene glycol di-succinimidyl succinate, pentaerythritol poly(ethylene glycol) ether tetrasuccinimidyl glutarate, succinimidized poly-L-glutamic acid, an aldehyde group-introduced starch, and an aldehyde group-introduced dextran, it can be dissolved in a water solvent with high dispersability. Moreover, it is possible to bond tissues by crosslinking the amino groups of the hydrophobically modified, gelatin and the amino groups of proteins such as collagen or the like existing in the biological tissue with crosslinking reagents which have active ester groups or acid anhydrides in themolecule.

Since the tissue adhesive serving as an embodiment of the present invention is configured such that the water solvent used for the aqueous solution is a phosphate buffer solution (PBS) having a pH of from 6.0 to 8.0, the time before the solidification can be appropriately set.

Since the tissue adhesive serving as an embodiment of the present invention is configured to include a fish-derived gelatin in which the number of hydroxyproline per 1000 constitutional amino acids thereof is 90 or less, aggregation of hydrophobic groups can be inhibited and the bonding strength of the tissue adhesive can be improved.

Since the method for producing a tissue adhesive serving as an embodiment of the present invention is configured such that the method includes a step of adding an organic molecule having a hydrophobic group to a solution in which a fish-derived gelatin in which the number of hydroxyproline per 1000 constitutional amino acids is 90 or less is dissolved to substitute a part of the amino groups on a side chain of the fish-derived gelatin, thereby synthesizing a hydrophobically modified, fish-derived gelatin, a step of dispersing the hydrophobically modified, fish-derived gelatin in a phosphate buffer solution, thereby preparing an adhesive component composed of an aqueous solution containing the hydrophobically modified, fish-derived gelatin, and a step of dispersing a water-soluble crosslinking reagent, the molecular main chain of which includes an amide linkage or an ethylene glycol unit or a sugar chain and which has two or more of an active ester group or an acid anhydride or an aldehyde group, in a phosphate buffer solution, thereby preparing a curative component composed of an aqueous solution of the water-soluble crosslinking reagent, it is possible to prepare a tissue adhesive by dispersing the hydrophobically modified, fish-derived gelatin and the water-soluble crosslinking reagent uniformly in an aqueous solution and easily prepare a tissue adhesive being high in bonding strength, stable in bonding properties, and excellent in spreadability.

The method for producing a tissue adhesive serving as an embodiment of the present invention is configured to include a step of adding an organic molecule having a hydrophobic group to a solution in which a fish-derived gelatin in which the number of hydroxyproline per 1000 constitutional amino acids is 90 or less is dissolved to substitute a part of the amino groups on a side chain of the fish-derived gelatin, thereby synthesizing a hydrophobically modified, fish-derived gelatin, a step of dispersing the hydrophobically modified, fish-derived gelatin in a phosphate buffer solution, thereby preparing an aqueous solution containing the hydrophobically modified, fish-derived gelatin, and a step of dispersing the fish-derived gelatin in a phosphate buffer solution, thereby preparing an aqueous solution containing the fish-derived gelatin, a step of mixing the aqueous solution containing the hydrophobically modified, fish-derived gelatin with the aqueous solution containing the fish-derived gelatin, thereby preparing an adhesive component composed of a mixed solution, and a step of dispersing a water-soluble crosslinking reagent, the molecular main chain of which includes an amide linkage or an ethylene glycol unit or a sugar chain and which has two or more of an active ester group or an acid anhydride or an aldehyde group, in a phosphate buffer solution, thereby preparing a curative component composed of an aqueous solution containing the water-soluble crosslinking reagent, it is possible to prepare a tissue adhesive by dispersing the hydrophobically modified, fish-derived gelatin and the water-soluble crosslinking reagent uniformly in an aqueous solution and easily prepare a tissue adhesive being high in bonding strength, stable in bonding properties, and excellent in spreadability. In addition, aggregation of hydrophobic groups can be inhibited and the bonding strength of a tissue adhesive can be improved.

Since the method for producing a tissue adhesive serving as an embodiment of the present invention is configured such that an adhesive component composed of the mixed solution is prepared by adjusting the weight ratio of the solution containing the hydrophobically modified, fish-derived gelatin to the aqueous solution containing the fish-derived gelatin to not less than 1:9 and less than 5:5, aggregation of hydrophobic groups can be inhibited and the bonding strength of a tissue adhesive can be improved.

The tissue adhesive and the method for producing the same serving as the embodiments of the present invention are not limited to the above-mentioned embodiments, and they may be executed with various modifications within the scope of the technical idea of the present invention. Specific examples of these embodiments are shown in the following Examples. However, the present invention is not to be limited to these Examples.

EXAMPLES

Test Example 1

<Preparation of Gltn/4S-PEG Tissue Adhesive for Evaluation of Dependency on Concentration of Water-Soluble Crosslinking Reagent (4S-PEG)>

First, a tilapia scale-derived fish gelatin (abbreviation: Gltn, MW: 70,000, hydroxyproline content: 79 units per 1000 amino acids, produced by Nitta Gelatin Inc.) as a fish gelatin, pentaerythritol poly(ethylene glycol) ether tetrasuccinimidyl glutarate (abbreviation: 4S-PEG, MW: 10,000, produced by NOF Corporation), and a physiological saline (produced by Otsuka Pharmaceutical Co., Ltd.) as a water-soluble crosslinking reagent were prepared.

Then, a 0.1 M, pH 7.0 phosphate buffered saline (abbreviation: PBS) was prepared.

Then, a gelatin solution (Gltn solution) was prepared by dissolving the Gltn in the 0.1 M PBS (pH 7.0) so that the Gltn concentration might be 40 wt %.

Then, five 4S-PEG solutions having concentrations of 5, 7.5, 10, 15, and 17 mM, respectively, were prepared by dissolving prescribed amounts of the 4S-PEG in the 0.1 M PBS (pH 7.0).

Then, tissue adhesives of Test Examples 1-1 to 1-5 were prepared by mixing the Gltn solution with each of the five 4S-PEG solutions in a volume ratio of 1:1.

Next, these tissue adhesives were pre-incubated at 37° C. beforehand and then were subjected to a bonding strength measurement.

<Bonding Strength Measurement (Shear Tensile Measurement)>

A bonding strength measurement by measurement of the shear tensile of a tissue adhesive was carried out.

Figure 4:
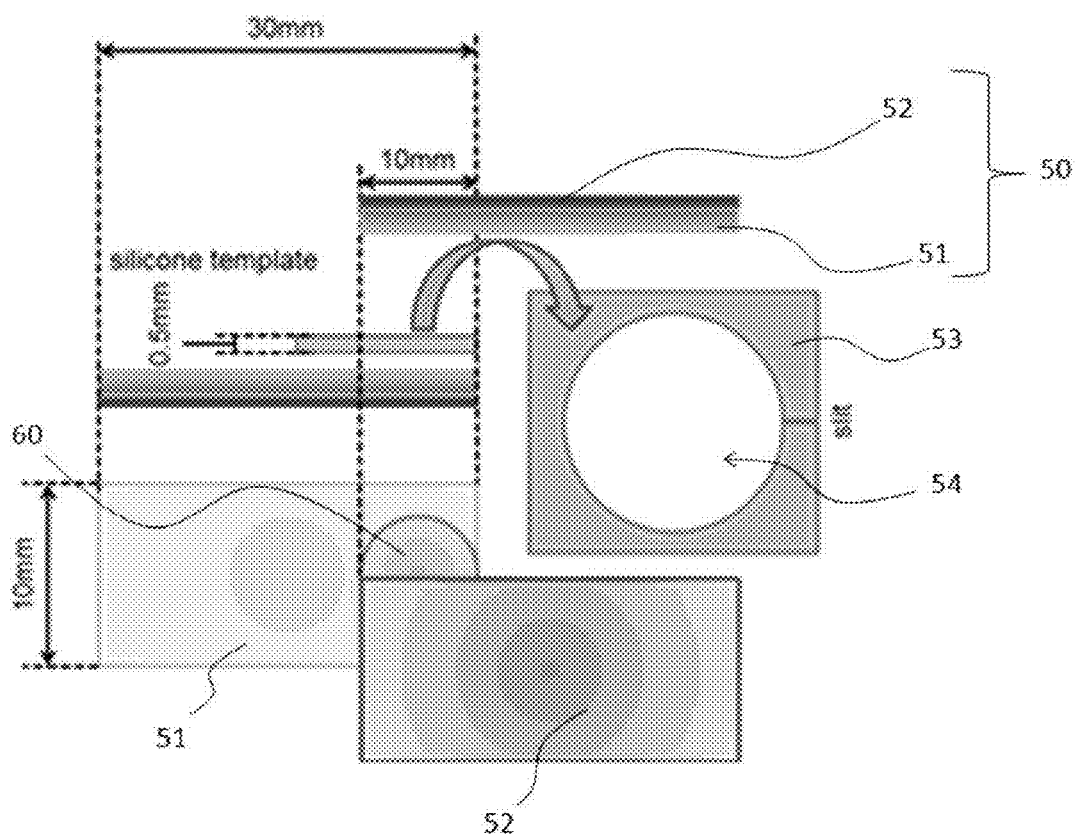
FIG. 4 is a schematic diagram of a bonding strength measurement.
Figure 5:
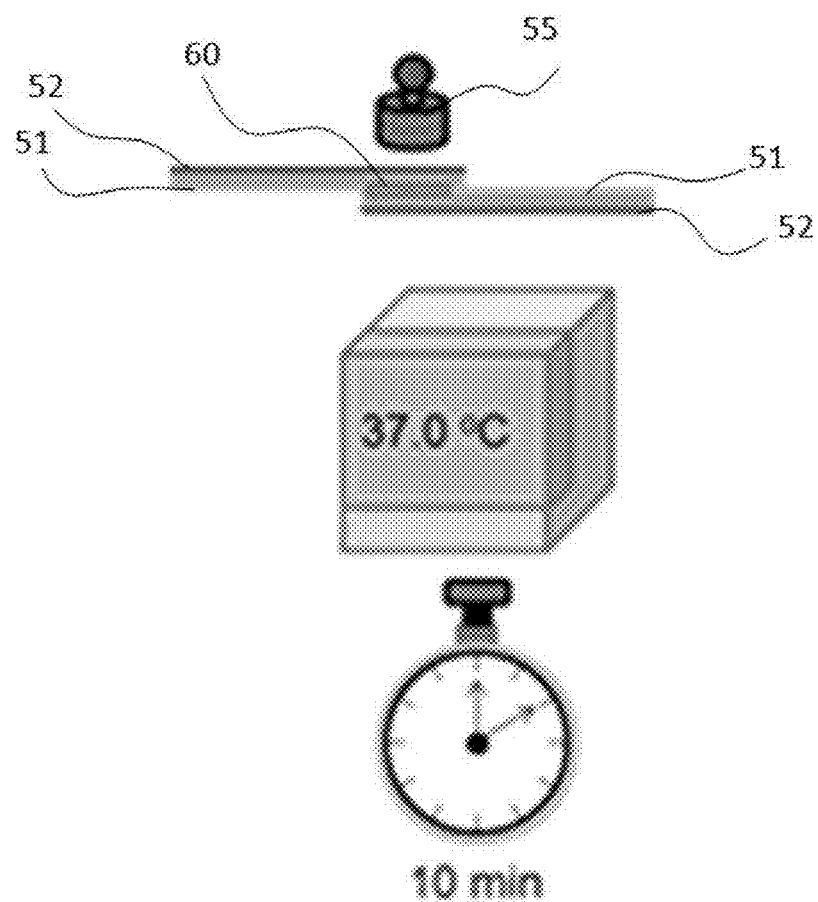
FIG. 5 is a schematic diagram of a bonding strength measurement.
Figure 6:
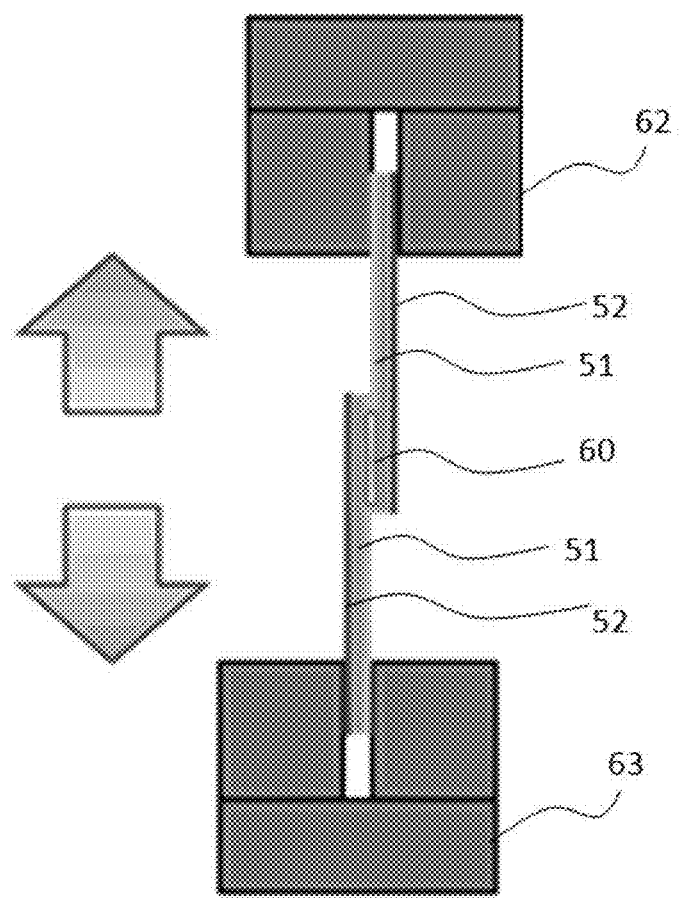
FIG. 6 is a schematic diagram of a bonding strength measurement.

FIGS. 4 to 6 are schematic diagrams of a bonding strength measurement.

First, two porcine vascular membranes 50 (10 mm×30 mm) were prepared. In each of the porcine vascular membranes 50, one side was named a media 51 and the other side was named an adventitia 52.

Then, as illustrated in FIG. 4, a mask 53 made of a 0.5-mm thick silicon sheet being square in plan and sized about 12 mm on each side was placed on the media 51 at one end of one of the porcine vascular membranes 50. The mask 53 was provided with a hole 54 having a circular shape in plan being 10 mm in diameter. The mask 53 was provided at one side with a slit leading to the hole 54.

Them, a tissue adhesive 60 was dropped on the media 51 exposed in the hole 54.

Then, one end of the other porcine vascular membrane 50 was placed immediately such that the media 51 might be mutually superposed via the tissue adhesive 60.

Then, as illustrated in FIG. 5, a 50-gram weight 55 was placed on the superimposed porcine vascular membranes 50.

Then, the sample was incubated at 37° C. for 10 minutes.

Immediately after the incubation, as illustrated in FIG. 6, the other ends of the porcine vascular membranes 50 were cramped and fixed to supporters 62, 63, respectively, and then they were drawn in opposing directions, so that shear tensile measurement was carried out with a Texture Analyzer (manufactured by EKO Instruments Co., Ltd.).

<Results of Evaluation of Dependency of Bonding Strength on Concentration of Water-Soluble Crosslinking Reagent (4S-PEG)>

It is assumed that the 4S-PEG used as a water-soluble crosslinking reagent causes salting-out in the presence of a salt and the bulk strength after crosslinking will lower. Therefore, the dependency of bonding strength on the concentration of the water-soluble crosslinking reagent (4S-PEG) was measured. The tilapia scale-derived fish gelatin (Gltn) was dissolved in a solvent that was a 0.1 M PBS adjusted to pH 7.0.

Figure 7:
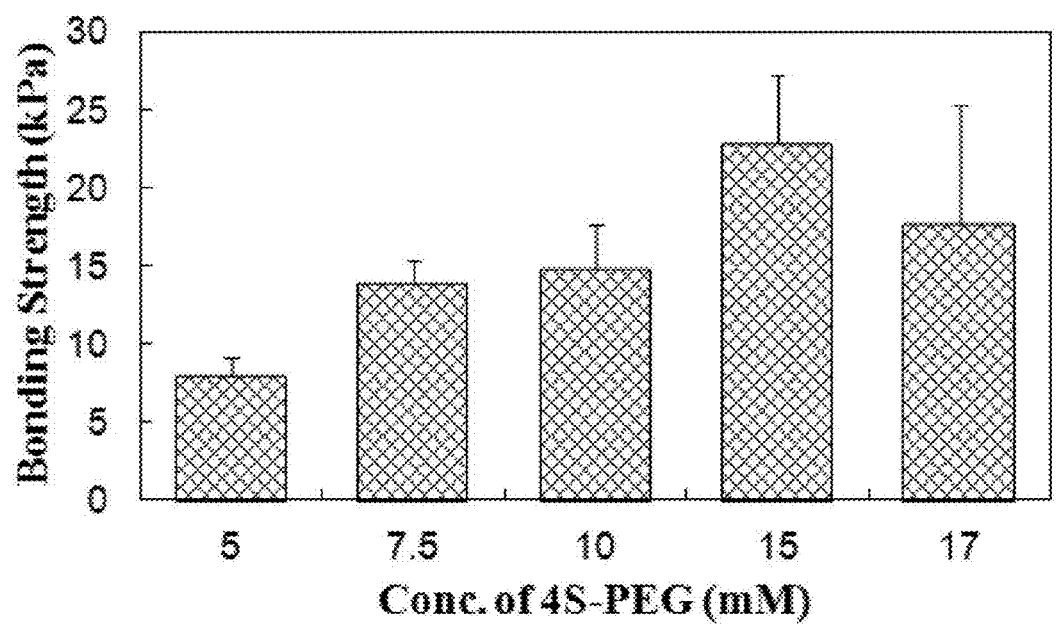
FIG. 7 is a graph of the dependency of bonding strength on the concentration of a water-soluble crosslinking reagent (4S-PEG).

The result (the dependency of bonding strength on the concentration of the water-soluble crosslinking reagent (4S-PEG)) shown in FIG. 7 was obtained. As shown in FIG. 7, the adhesion strength exhibited a local maximum value when the 4S-PEG concentration was 15 mM.

From the fact that the amount of the residual amino groups of the Gltn was determined to be 169.64 μmol/g by a trinitrobenzenesulfonic acid method, the condition for amino groups:succinimidyl groups=1:1 is a 4S-PEG concentration of 17 mM. Therefore, it was presumed that the bonding strength became locally maximum by producing a state where the material was crosslinked so as to achieve amino groups:succinimidyl groups=1:1.

Test Example 2

<Preparation of Gltn/4S-PEG Tissue Adhesive for Evaluation of Dependency on Solvent pH Value>

First, 40 wt % solutions of a tilapia scale-derived fish gelatin (Gltn) were prepared using solvents each being a 0.1 M PBS adjusted to pH 6.0, 6.5, 7.0, or 7.5.

Then, 4.5 mM 4S-PEG solutions were prepared using solvents each being a 0.1 M PBS adjusted to pH 6.0, 6.5, 7.0, or 7.5.

Then, tissue adhesives of Test Examples 2-1 to 2-4 were prepared each by mixing a Gltn solution with a 4S-PEG solution having the same pH value, in a volume ratio of 1:1.

Next, these tissue adhesives were pre-incubated at 37° C. beforehand and then were subjected to a bonding strength measurement.

In addition, for comparison, the bonding strength of a commercially available tissue adhesive (Gelatin Resorcinol Formaldehyde: expressed as GRF) composed of gelatin and formaldehyde was also measured.

<Results of Evaluation of Dependency of Bonding Strength on Solvent (PBS) pH Value>

The crosslinking reaction of this tissue adhesive is a nucleophilic substitution reaction of the amino groups of gelatin to the active ester groups of 4S-PEG, and the reaction rate thereof depends on the protonation of the amino groups, i.e., the pH value of the solvent. For this reason, the dependency of bonding strength on a solvent (PBS) pH value was measured.

Figure 8:
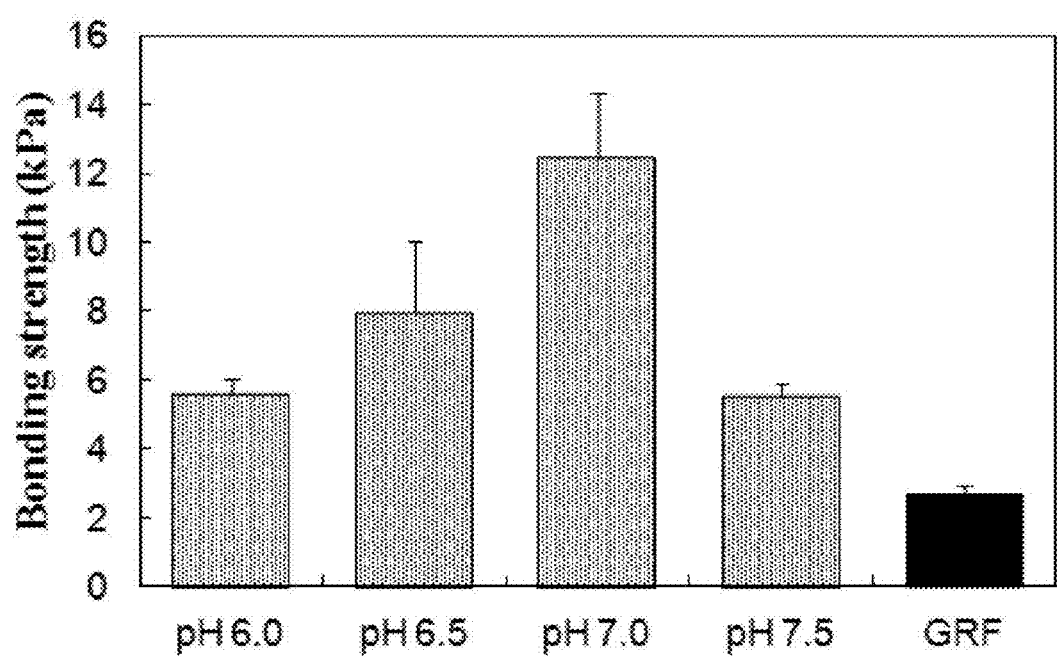
FIG. 8 is a graph of the dependency of bonding strength on the pH value of a solvent (PBS).
Figure 9:
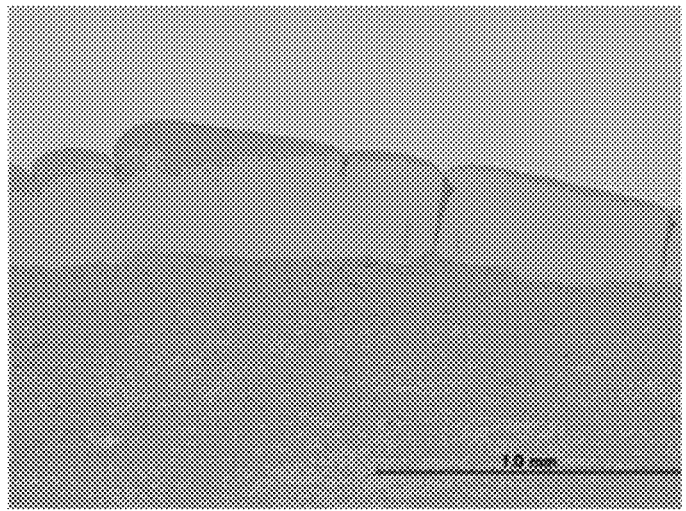
FIG. 9 is a cross-sectional image of a tissue stained with hematoxylin and eosin after a bonding strength measurement using the adhesive of Test Example 2-1
The conditions for the preparation of the adhesive of Test Example 2-1 include Gltn 40 wt % soln. 4S-PEG 4.5 mM (0.1 M PBS pH 6.0).
Figure 10:
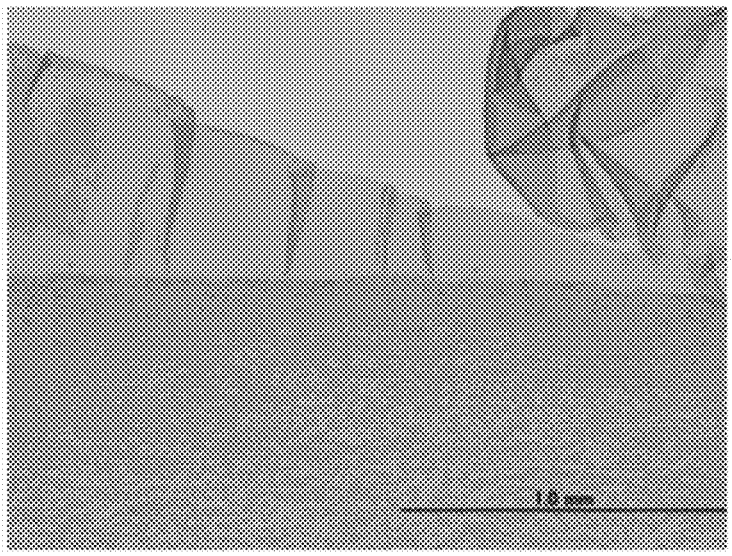
FIG. 10 is a cross-sectional image of a tissue stained with hematoxylin and eosin after a bonding strength measurement using the adhesive of Test Example 2-2.
The conditions for the preparation of the adhesive of Test Example 2-2 include Gltn 40 wt % soln. 4S-PEG 4.5 mM (0.1 M PBS pH 6.5).
Figure 12:
FIG. 12 is a cross-sectional image of a tissue stained with hematoxylin and eosin after a bonding strength measurement using the adhesive of Test Example 2-4.
The conditions for the preparation of the adhesive of Test Example 2-4 include Gltn 40 wt % soln. 4S-PEG 4.5 mM (0.1 M PBS pH 7.5).

The result (the dependency of bonding strength on a solvent (PBS) pH value) shown in FIG. 8 was obtained. As shown in FIG. 8, the bonding strength exhibited a local maximum value when the pH value of the solvent (PBS) was 7.0.

In addition, FIG. 9 to FIG. 12 are cross-sectional images of the tissues stained with hematoxylin and eosin after bonding strength measurements using the adhesives of Test Example 2-1 to 2-4, respectively. The preparation conditions for the individual adhesives are Gltn 40 wt % soln. 4S-PEG 4.5 mM (0.1 M PBS pH 6.0 (Test Example 2-1), 6.5 (Test Example 2-2), 7.0 (Test Example 2-3), 7.5 (Test Example 2-4)).

Figure 13:
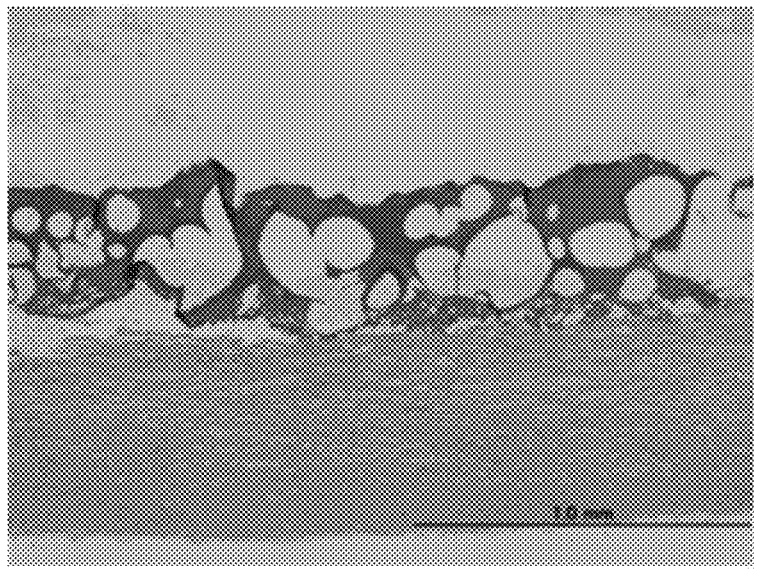
FIG. 13 is a cross-sectional image of a tissue stained with hematoxylin and eosin after a bonding strength measurement using GRF.

For comparison, a cross-sectional image of a tissue stained with hematoxylin and eosin after a bonding strength measurement using GRF is shown in FIG. 13.

In all of FIG. 9 to FIG. 13, the cured adhesive (upper part) observed was broken.

Example 1

<Preparation of 4Chol-Gltn/Gltn (1:9)/4S-PEG Tissue Adhesive>

First, hydrophobically modified, a tilapia scale-derived fish gelatin (Chol-Gltn), at a hydrophobic group (Chol) introduction ratio of 4 mol % relative to all the amino groups in the Gltn was prepared.

Then, a 40 wt % solution of a hydrophobically modified, tilapia scale-derived fish gelatin (4Chol-Gltn) was prepared using a solvent being a 0.1 M PBS adjusted to pH 7.0.

Then, a 40 wt % solution of a tilapia scale-derived fish gelatin (Gltn) was prepared using a solvent being a 0.1 M PBS adjusted to pH 7.0.

Then, a mixed solution was prepared so that a mixture ratio (weight ratio) of Chol-Gltn solution:Gltn solution=1:9 might be attained.

Then, a 15 mM 4S-PEG solution was prepared using a solvent being a 0.1 M PBS adjusted to pH 7.0.

Then, a tissue adhesive of Example 1 was prepared by mixing the mixed solution and the 4S-PEG solution in a volume ratio of 1:1.

Next, this tissue adhesive was pre-incubated at 37° C. beforehand and then was subjected to a bonding strength measurement at bonding times of 1, 3, 5, 10, 15, 30, and 45 (min).

<Results of Evaluation of Dependency of Bonding Strength on Bonding Time>

Figure 14:
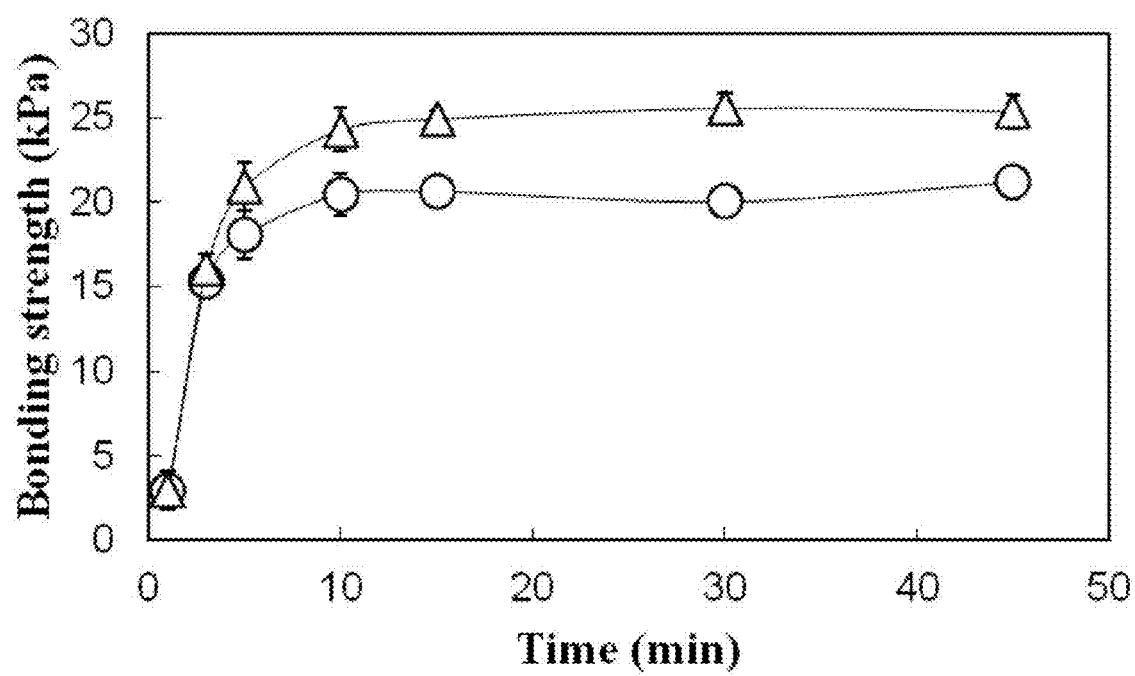
FIG. 14 is a graph of the dependency of bonding strength on adhesion time.

The result (the dependency of bonding strength on bonding time) shown in FIG. 14 was obtained. As shown in FIG. 14, the bonding strength became almost the maximum and saturated at a bonding time of 10 minutes and even though the bonding time was further elongated, the bonding strength did not vary significantly.

Example 2

<Preparation of 0, 4, 7, 23, and 70Chol-Gltn/4S-PEG Tissue Adhesives>

First, a hydrophobically modified, tilapia scale-derived fish gelatin (Chol-Gltn) at hydrophobic group (Chol group) introduction ratios of 4, 7, 23, and 70 mol % relative to all the amino groups in the Gltn were prepared. In addition, an hydrophobically unmodified, tilapia scale-derived fish gelatin was also subjected to evaluation, which is expressed as 0Chol-Gltn.

Then, 40 wt % solutions of the hydrophobically unmodified, tilapia scale-derived fish gelatin (0Chol-Gltn) and the hydrophobically modified, tilapia scale-derived fish gelatins (4, 7, 23, 70Chol-Gltn) were prepared using a solvent being a 0.1 M PBS adjusted to pH 7.4.

Then, a 4.5 mM 4S-PEG solution was prepared using a solvent being a 0.1 M PBS adjusted to pH 7.4.

Then, tissue adhesives of Examples 2-1 to 2-5 were prepared by mixing each of the five Chol-Gltn solutions with a 4S-PEG solution in a volume ratio of 1:1.

Next, these tissue adhesives were pre-incubated at 37° C. beforehand and then were subjected to a bonding strength measurement.

In addition, for comparison, the bonding strength of a commercially available tissue adhesive (Gelatin Resorcinol Formaldehyde: expressed as GRF) composed of gelatin and formaldehyde was also measured.

<Results of Evaluation of Dependency of Bonding Strength on Hydrophobic Group (Chol Group) Introduction Ratio>

This research has intended to create Chol-Gltn/4S-PEG with which a hydrophobic group (Chol group) has a tissue penetrating capability to a hydrophobic region of ECM. For this reason, evaluation of the bonding strength of tissue adhesives prepared by mixing each of 40 wt % solutions of 0, 4, 7, 23, and 70Chol-Gltn with a 4S-PEG solution in a volume ratio 1:1 was carried out and thereby the dependency of bonding strength on hydrophobic group (Chol group) introduction ratio was evaluated.

Figure 15:
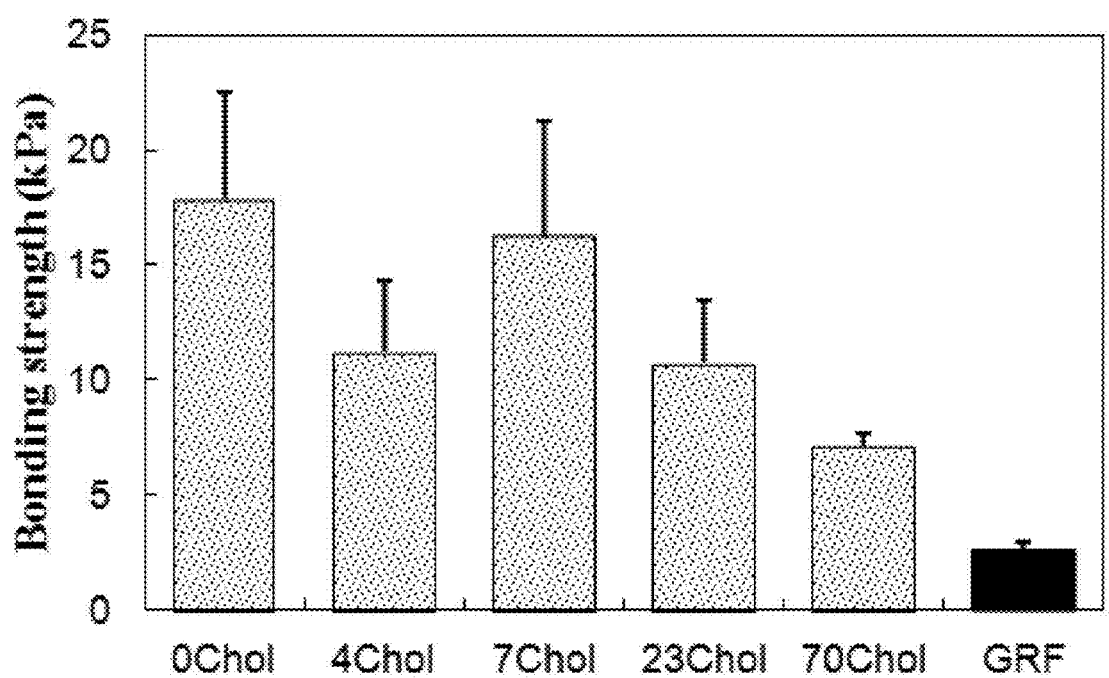
FIG. 15 is a graph of the dependency of bonding strength on the introduction ratio of hydrophobic groups (Chol groups).
Figure 17:
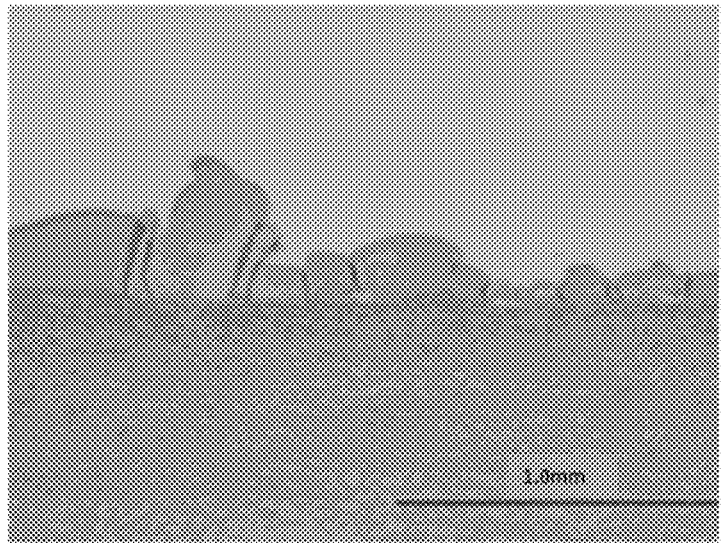
FIG. 17 is a cross-sectional image of a tissue stained with hematoxylin and eosin after a bonding strength measurement using the adhesive of Example 3-1.
The conditions for the preparation of the adhesive of Example 3-1 include 4Chol-Gltn/Gltn=0:10 40 wt % soln. (0.1M PBS pH 7.4), and 4S-PEG 4.5 mM (0.1M PBS pH 7.4).
Figure 18:
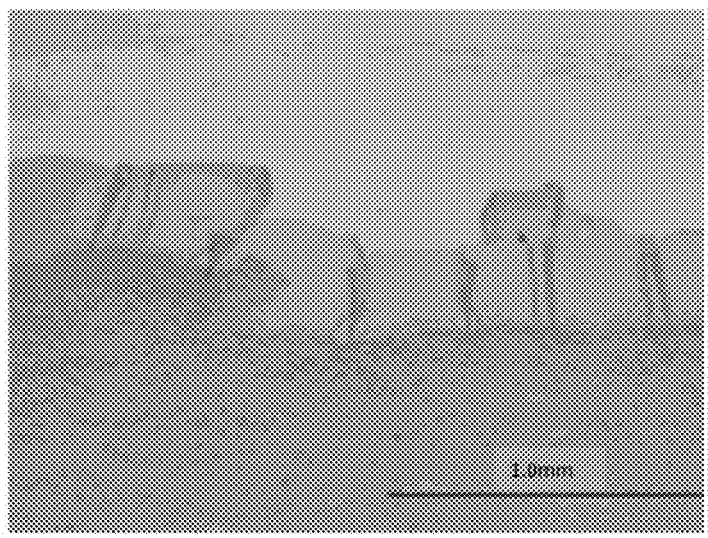
FIG. 18 is a cross-sectional image of a tissue stained with hematoxylin and eosin after a bonding strength measurement using the adhesive of Example 3-2.
The conditions for the preparation of the adhesive of Example 3-2 include 4Chol-Gltn/Gltn=1:9 40 wt % soln. (0.1M PBS pH 7.4), and 4S-PEG 4.5 mM (0.1M PBS pH 7.4).
Figure 19:
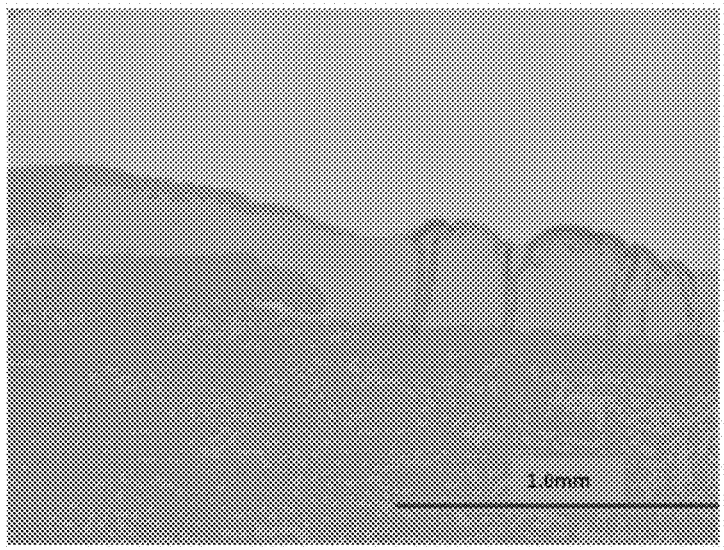
FIG. 19 is a cross-sectional image of a tissue stained with hematoxylin and eosin after a bonding strength measurement using the adhesive of Example 3-3.
The conditions for the preparation of the adhesive of Example 3-3 include 4Chol-Gltn/Gltn=3:7 40 wt % soln. (0.1M PBS pH 7.4), and 4S-PEG 4.5 mM (0.1M PBS pH 7.4).
Figure 20:
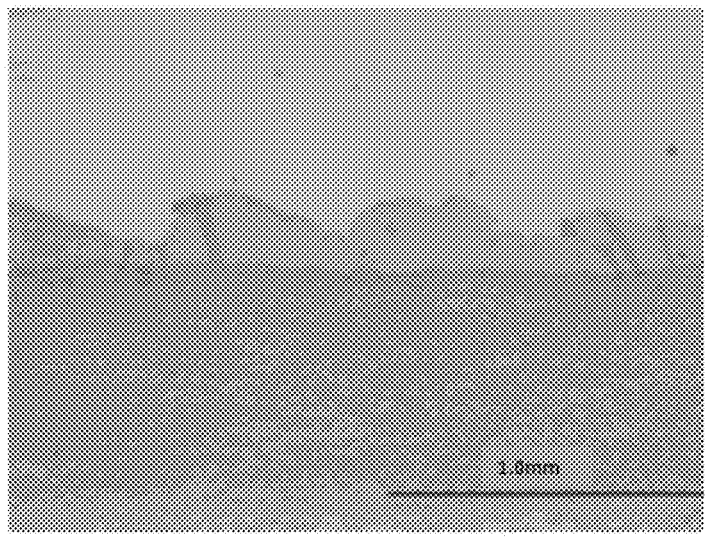
FIG. 20 is a cross-sectional image of a tissue stained with hematoxylin and eosin after a bonding strength measurement using the adhesive of Example 3-4.
The conditions for the preparation of the adhesive of Example 3-4 include 4Chol-Gltn/Gltn=5:5 40 wt % soln. (0.1M PBS pH 7.4), and 4S-PEG 4.5 mM (0.1M PBS pH 7.4).
Figure 21:
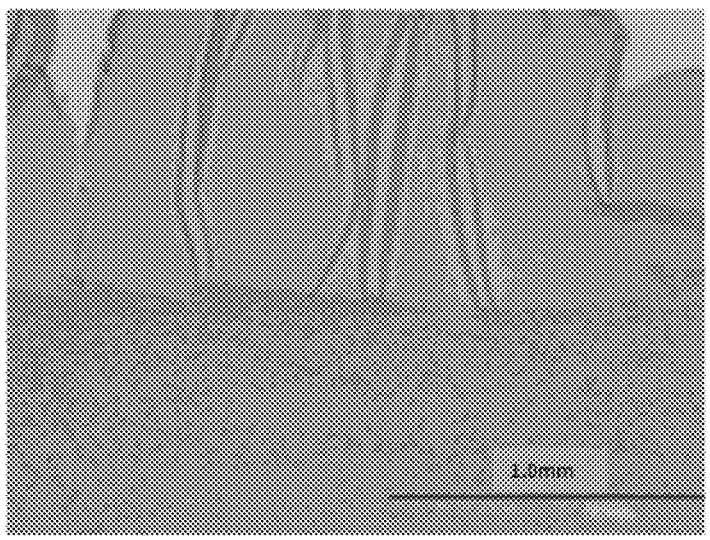
FIG. 21 is a cross-sectional image of a tissue stained with hematoxylin and eosin after a bonding strength measurement using the adhesive of Example 3-5.

The result (the dependency of bonding strength on hydrophobic group (Chol group) introduction ratio) shown in FIG. 15 was obtained.

As shown in FIG. 15, 4, 7, 23, and 70Chol-Gltns exhibited lower bonding strengths than 0Chol-Gltn. Among the hydrophobically modified, gelatins, the bonding strength of 7Chol-Gltn was the highest, and 4Chol-Gltn and 23Chol-Gltn were second highest in bonding strength.

It is believed that the reason for this result was that the introduced Chol groups aggregated and failed to contribute to the permeability into a tissue and that the bulk strength of the tissue adhesive was lowered by the aggregation.

Mixing of Gltn with Chol-Gltn can inhibit the aggregation of Chol groups and may potentially enhance the bonding strength of the tissue adhesive. For this reason, experiments in which the mixture ratio of the Chol-Gltn solution and the Gltn solution was varied were carried out in Examples 5 and 6.

Example 3

<Preparation of 4Chol-Gltn/Gltn (0:10 to 9:1)/4S-PEG Tissue Adhesive>

First, a 40 wt % solution of 4Chol-Gltn was prepared using a solvent being a 0.1 M PBS adjusted to pH 7.4.

Then, a 40 wt % solution of a tilapia scale-derived fish gelatin (Gltn) was prepared using a solvent being a 0.1 M PBS adjusted to pH 7.4.

Then, six mixed solutions were prepared while adjusting the weight ratio of the 4Chol-Gltn solution to the Gltn solution to 0:10, 1:9, 3:7, 5:5, 7:3, and 9:1.

Then, a 4.5 mM 4S-PEG solution was prepared using a solvent being a 0.1 M PBS adjusted to pH 7.4.

Then, each of the six Chol-Gltn solutions and the 4S-PEG solution were mixed in a volume ratio of 1:1.

The tissue adhesives of Examples 3-1 to 3-6 were thereby prepared.

These tissue adhesives were pre-incubated at 37° C. beforehand and then were subjected to a bonding strength measurement.

In addition, for comparison, the bonding strength of a commercially available tissue adhesive (Gelatin Resorcinol Formaldehyde: expressed as GRF) composed of gelatin and formaldehyde was also measured.

<Result of Evaluation of the Dependency of Bonding Strength on the Weight Ratio of 4Chol-Gltn Solution to Gltn Solution>

The result (the dependency of bonding strength on the weight ratio of the 4Chol-Gltn solution to the Gltn solution) shown in FIG. 16 was obtained.

As shown in FIG. 16, the highest bonding strength was exhibited at a time of 4Chol-Gltn solution:Gltn solution=1:9 (weight ratio). In addition, the sample of 5:5 (weight ratio) exhibited a higher bonding strength than the sample of Gltn alone.

FIGS. 17 to 22 are cross-sectional images of the tissues stained with hematoxylin and eosin after bonding strength measurements using the adhesives of Example 3-1 to 3-5, respectively.

The preparation conditions for the individual adhesives are 4Chol-Gltn/Gltn=0:10 (Example 3-1), 1:9 (Example 3-2), 3:7 (Example 3-3), 5:5 (Example 3-4), 7:3 (Example 3-5), 9:1 (Example 3-6), 40 wt % soln. (0.1 M PBS pH 7.4), and 4S-PEG 4.5 mM (0.1 M PBS pH 7.4).

In all of FIG. 17 to FIG. 22, the cured adhesive (upper part) observed was broken.

Example 4

<Preparation of 7Chol-Gltn/Gltn (0:10 to 9:1)/4S-PEG Tissue Adhesive>

First, a 40 wt % solution of 7Chol-Gltn and Gltn was prepared using a solvent being a 0.1 M PBS adjusted to pH 7.4.

Then, a 40 wt % solution of a tilapia scale-derived fish gelatin (Gltn) was prepared using a solvent being a 0.1 M PBS adjusted to pH 7.4.

Then, six mixed solutions were prepared while adjusting the weight ratio of the 7Chol-Gltn solution to the Gltn solution to 0:10, 1:9, 3:7, 5:5, 7:3, and 9:1.

Then, a 4.5 mM 4S-PEG solution was prepared using a solvent being a 0.1 M PBS adjusted to pH 7.4.

Then, six mixed solutions were prepared while adjusting the weight ratio of the 7Chol-Gltn solution to the Gltn solution to 0:10, 1:9, 3:7, 5:5, 7:3, and 9:1.

Then, tissue adhesives of Examples 4-1 to 4-6 were prepared by mixing each of the six Chol-Gltn solutions with a 4S-PEG solution in a volume ratio of 1:1.

These tissue adhesives were pre-incubated at 37° C. beforehand and then were subjected to a bonding strength measurement.

In addition, for comparison, the bonding strength of a commercially available tissue adhesive (Gelatin Resorcinol Formaldehyde: expressed as GRF) composed of gelatin and formaldehyde was also measured.

<Result of Evaluation of the Dependency of Bonding Strength on the Weight Ratio of 7Chol-Gltn Solution to Gltn Solution>

The result (the dependency of bonding strength on the weight ratio of the 7Chol-Gltn solution to the Gltn solution) shown in FIG. 23 was obtained.

As shown in FIG. 23, the highest bonding strength was exhibited at a time of 7Chol-Gltn solution:Gltn solution=1:9 (weight ratio). In addition, the sample of 5:5 (weight ratio) exhibited a higher bonding strength than the sample of Gltn alone.

Example 5

<Preparation of 4Chol-Gltn/Gltn (0:10, 1:9, 5:5)/4S-PEG Tissue Adhesives>

First, a hydrophobically modified tilapia scale-derived fish gelatin (4Chol-Gltn), at a hydrophobic group (Chol) introduction ratio of 4% was prepared.

Then, a 40 wt % solution of a hydrophobically modified tilapia scale-derived fish gelatin (4Chol-Gltn) was prepared using a solvent being a 0.1 M PBS adjusted to pH 7.0.

Then, a 40 wt % solution of a tilapia scale-derived fish gelatin (Gltn) was prepared using a solvent being a 0.1 M PBS adjusted to pH 7.0.

Then, three mixed solutions were prepared so that mixture ratios (weight ratios) of 4Chol-Gltn solution:Gltn solution=0:10, 1:9, 5:5 might be attained.

Then, a 15 mM 4S-PEG solution was prepared using a solvent being a 0.1 M PBS adjusted to pH 7.0.

Then, tissue adhesives of Examples 5-1 to 5-3 were prepared by mixing each of the three mixed solutions with a 4S-PEG solution in a volume ratio of 1:1.

These tissue adhesives were pre-incubated at 37° C. beforehand and then were subjected to a bonding strength measurement.

In addition, for comparison, the bonding strength of a commercially available tissue adhesive (Gelatin Resorcinol Formaldehyde: expressed as GRF) composed of gelatin and formaldehyde was also measured.

<Result of Evaluation of the Dependency of Bonding Strength on the Weight Ratio of 4Chol-Gltn Solution to Gltn Solution>

The result (the dependency of bonding strength on the weight ratio of the 4Chol-Gltn solution to the Gltn solution) shown in FIG. 24 was obtained.

As shown in FIG. 24, the highest bonding strength was exhibited at a time of 4Chol-Gltn solution:Gltn solution=1:9 (weight ratio).

Example 6

<Preparation of 7Chol-Gltn/Gltn (0:10, 1:9, 5:5)/4S-PEG Tissue Adhesives>

First, a hydrophobically modified tilapia scale-derived fish gelatin (7Chol-Gltn) at a hydrophobic group (Chol) introduction ratio of 7% was prepared.

Then, a 40 wt % solution of a hydrophobically modified tilapia scale-derived fish gelatin (7Chol-Gltn) was prepared using a solvent being a 0.1 M PBS adjusted to pH 7.0.

Then, a 40 wt % solution of a tilapia scale-derived fish gelatin (Gltn) was prepared using a solvent being a 0.1 M PBS adjusted to pH 7.0.

Then, three mixed solutions were prepared so that mixture ratios (weight ratios) of 7Chol-Gltn solution:Gltn solution=0:10, 1:9, 5:5 might be attained.

Then, a 15 mM 4S-PEG solution was prepared using a solvent being a 0.1 M PBS adjusted to pH 7.0.

Then, tissue adhesives of Examples 6-1 to 6-3 were prepared by mixing each of the three mixed solutions with a 4S-PEG solution in a volume ratio of 1:1.

These tissue adhesives were pre-incubated at 37° C. beforehand and then were subjected to a bonding strength measurement.

In addition, for comparison, the bonding strength of a commercially available tissue adhesive (Gelatin Resorcinol Formaldehyde: expressed as GRF) composed of gelatin and formaldehyde was also measured.

<Result of Evaluation of the Dependency of Bonding Strength on the Weight Ratio of 7Chol-Gltn Solution to Gltn Solution>

The result (the dependency of bonding strength on the weight ratio of the 7Chol-Gltn solution to the Gltn solution) shown in FIG. 25 was obtained.

As shown in FIG. 25, the highest bonding strength was exhibited at a time of 7Chol-Gltn solution:Gltn solution=1:9 (weight ratio).

Example 7

<Preparation of 23Chol-Gltn/Gltn (0:10, 1:9, 5:5)/4S-PEG Tissue Adhesives>

First, a hydrophobically modified tilapia scale-derived fish gelatin (23Chol-Gltn) at a hydrophobic group (Chol) introduction ratio of 23% was prepared.

Then, a 40 wt % solution of a hydrophobically modified tilapia scale-derived fish gelatin (23Chol-Gltn) was prepared using a solvent being a 0.1 M PBS adjusted to pH 7.0.

Then, a 40 wt % solution of a tilapia scale-derived fish gelatin (Gltn) was prepared using a solvent being a 0.1 M PBS adjusted to pH 7.0.

Then, three mixed solutions were prepared so that mixture ratios (weight ratios) of 23Chol-Gltn solution:Gltn solution=0:10, 1:9, 5:5 might be attained.

Then, a 15 mM 4S-PEG solution was prepared using a solvent being a 0.1 M PBS adjusted to pH 7.0.

Then, tissue adhesives of Examples 7-1 to 7-3 were prepared by mixing each of the three mixed solutions with a 4S-PEG solution in a volume ratio of 1:1.

These tissue adhesives were pre-incubated at 37° C. beforehand and then were subjected to a bonding strength measurement.

In addition, for comparison, the bonding strength of a commercially available tissue adhesive (Gelatin Resorcinol Formaldehyde: expressed as GRF) composed of gelatin and formaldehyde was also measured.

<Result of Evaluation of the Dependency of Bonding Strength on the Weight Ratio of 23Chol-Gltn Solution to Gltn Solution>

The result (the dependency of bonding strength on the weight ratio of the 23Chol-Gltn solution to the Gltn solution) shown in FIG. 26 was obtained.

As shown in FIG. 26, the highest bonding strength was exhibited at a time of 23Chol-Gltn solution:Gltn solution=0:10 (weight ratio).

Example 8

<Preparation of 70Chol-Gltn/Gltn (0:10, 1:9, 5:5)/4S-PEG Tissue Adhesives>

First, a tilapia scale-derived fish gelatin (70Chol-Gltn) hydrophobically modified, at a hydrophobic group (Chol) introduction ratio of 70% was prepared.

Then, a 40 wt % solution of a hydrophobically modified tilapia scale-derived fish gelatin (70Chol-Gltn) was prepared using a solvent being a 0.1 M PBS adjusted to pH 7.0.

Then, a 40 wt % solution of a tilapia scale-derived fish gelatin (Gltn) was prepared using a solvent being a 0.1 M PBS adjusted to pH 7.0.

Then, three mixed solutions were prepared so that mixture ratios (weight ratios) of 70Chol-Gltn solution:Gltn solution=0:10, 1:9, 5:5 might be attained.

Then, a 15 mM 4S-PEG solution was prepared using a solvent being a 0.1 M PBS adjusted to pH 7.0.

Then, tissue adhesives of Examples 8-1 to 8-3 were prepared by mixing each of the three mixed solutions with a 4S-PEG solution in a volume ratio of 1:1.

These tissue adhesives were pre-incubated at 37° C. beforehand and then were subjected to a bonding strength measurement.

In addition, for comparison, the bonding strength of a commercially available tissue adhesive (Gelatin Resorcinol Formaldehyde: expressed as GRF) composed of gelatin and formaldehyde was also measured.

<Result of Evaluation of the Dependency of Bonding Strength on the Weight Ratio of 70Chol-Gltn Solution to Gltn Solution>

The result (the dependency of bonding strength on the weight ratio of the 70Chol-Gltn solution to the Gltn solution) shown in FIG. 27 was obtained.

As shown in FIG. 27, the highest bonding strength was exhibited at the time of 70Chol-Gltn solution:Gltn solution=0:10 (weight ratio). The results shown in FIGS. 7 to 27 revealed that, regarding 4 to 70Chol-Gltns, a tissue adhesive having a weight ratio of 1:9 exhibited a higher bonding strength than a tissue adhesive having a weight ratio of 5:5.

FIG. 28 is a graph showing the dependency of the bonding strength of a tissue adhesive in a weight ratio of 1:9 on the hydrophobic group introduction ratio.

As shown in FIG. 28, at a weight ratio of 1:9, the bonding strength of the tissue adhesive of 7Chol-Gltn/Gltn took a local maximum.

None of the tissue adhesives prepared in the Examples were in a gel state and it was possible to use all of them in their original liquid state. Therefore, they were much higher in ease of handling than a tissue adhesive using a porcine gelatin having a molecular weight of about 20000.

The tissue adhesive prepared using the mixed solution of a 40 wt % solution (0.1 M PBS, pH 7.0) of 7Chol-Gltn/Gltn in a weight ratio of 1:9 and a 15 mM 4S-PEG solution (0.1 M PBS, pH 7.0) exhibited the highest bonding strength. The tissue adhesives prepared in the other Examples exhibited higher bonding strength than a commercially available GRF.

In Tables 1 to 5 are summarized the preparation conditions and the test conditions of the individual Test Examples and Examples.

TABLE 1

| | | Gelatin solution | | | | Solution of water-soluble crosslinking reagent | | | | Tissue adhesive Gelatin solution:water-soluble cross-linking reagent solution (volume ratio) | Test condition Adhesion time (minute) |
|---|---|---|---|---|---|---|---|---|---|---|---|
| | Name of tissue adhesive | Type of fish gelatin | Gelatin concentration (wt %) | Type of solvent | pH of solvent | Water-soluble crosslinking reagent | Type of solvent | pH of solvent | Concentration (mM) | | |
| Test Example 1-1 | Gltn/4S-PEG adhesive | Gltn | 40 | PBS (0.1M) | 7 | 4S-PEG | PBS (0.1M) | 7 | 5 | 1:1 | 10 |
| Test Example 1-2 | | | | | | | | | 7.5 | | |
| Test Example 1-3 | | | | | | | | | 10 | | |
| Test Example 1-4 | | | | | | | | | 15 | | |
| Test Example 1-5 | | | | | | | | | 17 | | |
| Test Example 2-1 | Gltn/4S-PEG adhesive | Gltn | 40 | PBS (0.1M) | 6 | 4S-PEG | PBS (0.1M) | 6 | 4.5 | 1:1 | 10 |
| Test Example 2-2 | | | | | 6.5 | | | 6.5 | | | |
| Test Example 2-3 | | | | | 7 | | | 7 | | | |

TABLE 1-continued

| | | Gelatin solution | | | | Solution of water-soluble crosslinking reagent | | | | Tissue adhesive Gelatin solution:water-soluble cross-linking reagent solution (volume ratio) | Test condition |
|---|---|---|---|---|---|---|---|---|---|---|---|
| | Name of tissue adhesive | Type of fish gelatin | Gelatin concentration (wt %) | Type of solvent | pH of solvent | Water-soluble crosslinking reagent | Type of solvent | pH of solvent | Concentration (mM) | | Adhesion time (minute) |
| Test Example 2-4 | | | | | 7.5 | | | 7.5 | | | |

\* Gltn: tilapia scale-derived fish gelatin

TABLE 2

| | | Gelatin solution | | | | Hydrophobically modified, gelatin solution | | | | | |
|---|---|---|---|---|---|---|---|---|---|---|---|
| | Name of tissue adhesive | Type of fish gelatin | Gelatin concentration (wt %) | Type of solvent | pH of solvent | Type of hydrophobically modified, fish gelatin | Hydrophobic group introduction ratio (%) | Hydrophobically modified, gelatin concentration (wt %) | Type of solvent | pH of solvent | |
| Example 1 | 4Chol-Gltn/ Gltn (1:9)/ 4S-PEG adhesive | Gltn | 40 | PBS (0.1M) | 7 | 4Chol-Gltn | 4 | 40 | PBS (0.1M) | 7 | |

| | | Mixed solution Hydrophobically modified, gelatin solution:gelatin solution (weight ratio) | Solution of water-soluble crosslinking reagent | | | | Tissue adhesive Mixed solution:water-soluble crosslinking reagent solution (volume ratio) | Test condition |
|---|---|---|---|---|---|---|---|---|
| | | | Water-soluble crosslinking reagent | Type of solvent | pH of solvent | Concentration (mM) | | Adhesion time (minute) |
| | Example 1 | 1:9 | 4S-PEG | PBS (0.1M) | 7 | 15 | 1:1 | 1 |
| | | | | | | | | 3 |
| | | | | | | | | 5 |
| | | | | | | | | 10 |
| | | | | | | | | 15 |
| | | | | | | | | 30 |
| | | | | | | | | 45 |

\* Gltn: tilapia scale-derived fish gelatin
\* Chol-Gltn: hydrophobically modified, tilapia scale-derived fish gelatin

TABLE 3

| | | Hydrophobically modified, gelatin solution | | | | |
|---|---|---|---|---|---|---|
| | Name of tissue adhesive | Type of hydrophobically modified, fish gelatin | Hydrophobic group introduction ratio (%) | Hydrophobically modified, gelatin concentration (wt %) | Type of solvent | pH of solvent |
| Example 2-1 | 0Chol-Gltn/ 4S-PEG adhesive | 0Chol-Gltn | 0 | 40 | PBS (0.1M) | 7.4 |
| Example 2-2 | 4Chol-Gltn/ 4S-PEG adhesive | 4Chol-Gltn | 4 | | | |
| Example 2-3 | 7Chol-Gltn/ 4S-PEG adhesive | 7Chol-Gltn | 7 | | | |
| Example 2-4 | 23Chol-Gltn/ 4S-PEG adhesive | 23Chol-Gltn | 23 | | | |
| Example 2-5 | 70Chol-Gltn/ 4S-PEG | 70Chol-Gltn | 70 | | | |

TABLE 3-continued

| | adhesive | | | | | |
|---|---|---|---|---|---|---|
| | | Solution of water-soluble crosslinking reagent | | | Tissue adhesive Hydrophobically modified, gelatin solution:solution of water-soluble crosslinking reagent (volume ratio) | Test condition |
| | Water-soluble crosslinking reagent | Type of solvent | pH of solvent | Concentration (mM) | | Adhesion time (minute) |
| Example 2-1 | 4S-PEG | PBS (0.1M) | 7.4 | 4.5 | 1:1 | 10 |
| Example 2-2 | | | | | | |
| Example 2-3 | | | | | | |
| Example 2-4 | | | | | | |
| Example 2-5 | | | | | | |

* Chol-Gltn: hydrophobically modified, tilapia scale-derived fish gelatin

TABLE 4

| | | Gelatin solution | | | | Hydrophobically modified, gelatin solution | | | | |
|---|---|---|---|---|---|---|---|---|---|---|
| | Name of tissue adhesive | Type of fish gelatin | Gelatin concentration (wt %) | Type of solvent | pH of solvent | Type of hydrophobically modified, fish gelatin | Hydrophobic group introduction ratio (%) | Hydrophobically modified, gelatin concentration (wt %) | Type of solvent | pH of solvent |
| Example 3-1 | 4Chol-Gltn/Gltn (0:10)/4S-PEG adhesive | Gltn | 40 | PBS (0.1M) | 7.4 | 4Chol-Gltn | 4 | 40 | PBS (0.1M) | 7.4 |
| Example 3-2 | 4Chol-Gltn/Gltn (1:9)/4S-PEG adhesive | | | | | | | | | |
| Example 3-3 | 4Chol-Gltn/Gltn (3:7)/4S-PEG adhesive | | | | | | | | | |
| Example 3-4 | 4Chol-Gltn/Gltn (5:5)/4S-PEG adhesive | | | | | | | | | |
| Example 3-5 | 4Chol-Gltn/Gltn (7:3)/4S-PEG adhesive | | | | | | | | | |
| Example 3-6 | 4Chol-Gltn/Gltn (9:1)/4S-PEG adhesive | | | | | | | | | |
| Example 4-1 | 7Chol-Gltn/Gltn (0:10)/4S-PEG adhesive | Gltn | 40 | PBS (0.1M) | 7.4 | 4Chol-Gltn | 7 | 40 | PBS (0.1M) | 7.4 |
| Example 4-2 | 7Chol-Gltn/Gltn (1:9)/4S-PEG adhesive | | | | | | | | | |
| Example 4-3 | 7Chol-Gltn/Gltn (3:7)/4S-PEG adhesive | | | | | | | | | |
| Example 4-4 | 7Chol-Gltn/Gltn (5:5)/4S-PEG adhesive | | | | | | | | | |
| Example 4-5 | 7Chol-Gltn/Gltn (7:3)/ | | | | | | | | | |

TABLE 4-continued

| | |
|---|---|
| Example 4-6 | 4S-PEG adhesive 7Chol-Gltn/ Gltn (9:1)/ 4S-PEG adhesive |

| | | Mixed solution Hydrophobically modified, gelatin solution:gelatin solution (weight ratio) | Solution of water-soluble crosslinking reagent | | | | Tissue adhesive Mixed solution:water-soluble cross-linking reagent solution (volume ratio) | Test condition |
|---|---|---|---|---|---|---|---|---|
| | | | Water-soluble crosslinking reagent | Type of solvent | pH of solvent | Concentration (mM) | | Adhesion time (minute) |
| | Example 3-1 | 0:10 | 4S-PEG | PBS (0.1M) | 7.4 | 4.5 | 1:1 | 10 |
| | Example 3-2 | 1:9 | | | | | | |
| | Example 3-3 | 3:7 | | | | | | |
| | Example 3-4 | 5:5 | | | | | | |
| | Example 3-5 | 7:3 | | | | | | |
| | Example 3-6 | 9:1 | | | | | | |
| | Example 4-1 | 0:10 | 4S-PEG | PBS (0.1M) | 7.4 | 4.5 | 1:1 | 10 |
| | Example 4-2 | 1:9 | | | | | | |
| | Example 4-3 | 3:7 | | | | | | |
| | Example 4-4 | 5:5 | | | | | | |
| | Example 4-5 | 7:3 | | | | | | |
| | Example 4-6 | 9:1 | | | | | | |

\* Gltn: tilapia scale-derived fish gelatin
\* Chol-Gltn: hydrophobically modified, tilapia scale-derived fish gelatin

TABLE 5

| | | Gelatin solution | | | | Hydrophobically modified, gelatin solution | | | | |
|---|---|---|---|---|---|---|---|---|---|---|
| | Name of tissue adhesive | Type of fish gelatin | Gelatin concentration (wt %) | Type of solvent | pH of solvent | Type of hydrophobically modified, fish gelatin | Hydrophobic group introduction ratio (%) | Hydrophobically modified, gelatin concentration (wt %) | Type of solvent | pH of solvent |
| Example 5-1 | 4Chol-Gltn/ Gltn (0:10)/ 4S-PEG adhesive | Gltn | 40 | PBS (0.1M) | 7 | 4Chol-Gltn | 4 | 40 | PBS (0.1M) | 7 |
| Example 5-2 | 4Chol-Gltn/ Gltn (1:9)/ 4S-PEG adhesive | | | | | | | | | |
| Example 5-3 | 4Chol-Gltn/ Gltn (5:5)/ 4S-PEG adhesive | | | | | | | | | |
| Example 6-1 | 7Chol-Gltn/ Gltn (0:10)/ 4S-PEG adhesive | Gltn | 40 | PBS (0.1M) | 7 | 7Chol-Gltn | 7 | 40 | PBS (0.1M) | 7 |
| Example 6-2 | 7Chol-Gltn/ Gltn (1:9)/ 4S-PEG adhesive | | | | | | | | | |
| Example 6-3 | 7Chol-Gltn/ Gltn (5:5)/ 4S-PEG adhesive | | | | | | | | | |

TABLE 5-continued

| Example | Tissue adhesive | | | | | | | | | |
|---|---|---|---|---|---|---|---|---|---|---|
| Example 7-1 | 23Chol-Gltn/Gltn (0:10)/4S-PEG adhesive | Gltn | 40 | PBS (0.1M) | 7 | 23Chol-Gltn | 23 | 40 | PBS (0.1M) | 7 |
| Example 7-2 | 23Chol-Gltn/Gltn (1:9)/4S-PEG adhesive | | | | | | | | | |
| Example 7-3 | 23Chol-Gltn/Gltn (5:5)/4S-PEG adhesive | | | | | | | | | |
| Example 8-1 | 70Chol-Gltn/Gltn (0:10)/4S-PEG adhesive | Gltn | 40 | PBS (0.1M) | 7 | 70Chol-Gltn | 70 | 40 | PBS (0.1M) | 7 |
| Example 8-2 | 70Chol-Gltn/Gltn (1:9)/4S-PEG adhesive | | | | | | | | | |
| Example 8-3 | 70Chol-Gltn/Gltn (5:5)/4S-PEG adhesive | | | | | | | | | |

| | Mixed solution Hydrophobically modified, gelatin solution:gelatin solution (weight ratio) | Solution of water-soluble crosslinking reagent | | | | Tissue adhesive Mixed solution:water-soluble cross-linking reagent solution (volume ratio) | Test condition |
|---|---|---|---|---|---|---|---|
| | | Water-soluble crosslinking reagent | Type of solvent | pH of solvent | Concentration (mM) | | Adhesion time (minute) |
| Example 5-1 | 0:10 | 4S-PEG | PBS (0.1M) | 7 | 15 | 1:1 | 10 |
| Example 5-2 | 1:9 | | | | | | |
| Example 5-3 | 5:5 | | | | | | |
| Example 6-1 | 0:10 | 4S-PEG | PBS (0.1M) | 7 | 15 | 1:1 | 10 |
| Example 6-2 | 1:9 | | | | | | |
| Example 6-3 | 5:5 | | | | | | |
| Example 7-1 | 0:10 | 4S-PEG | PBS (0.1M) | 7 | 15 | 1:1 | 10 |
| Example 7-2 | 1:9 | | | | | | |
| Example 7-3 | 5:5 | | | | | | |
| Example 8-1 | 0:10 | 4S-PEG | PBS (0.1M) | 7 | 15 | 1:1 | 10 |
| Example 8-2 | 1:9 | | | | | | |
| Example 8-3 | 5:5 | | | | | | |

* Gltn: tilapia scale-derived fish gelatin
* Chol-Gltn: hydrophobically modified, tilapia scale-derived fish gelatin (Example 9) Evaluation of Sealing Effect of Tissue Adhesive Composed of Hydrophobically Modified Cod Gelatin and 4S-PEG (1) Measurement of Pressure Resistance to Porcine Aorta
(1-1) Experimental Method The bonding strength to a porcine aorta of a tissue adhesive composed of an Hx-cGltn prepared by hexanoylizing a part of amino groups of cod gelatin (cGltn) and 4S-PEG was examined.

Specifically, the cod gelatin used was one having a molecular weight of 153,000 and a hydroxyproline content of 50 units per 1000 amino acids.

Then, a hydrophobically unmodified, 40% cGltn was prepared as an adhesive component (expressed as Org-cGltn solution or Org), an aqueous solution containing a water-soluble crosslinking agent 4S-PEG was prepared as a curative component (4S-PEG solution), and then a 1.0-mm thick sealant (tissue adhesive) was prepared by mixing 200 µl of the adhesive component with 200 µl of the curative component.

Likewise, hydrophobically unmodified, cGltns each having a hexanoyl group introduction ratio of 2.1 mol %, 8.5 mol %, or 18.3 mol % were prepared as an adhesive component (expressed as 2.1 Hx, 8.5 Hx, and 18.3 Hx), and then 1.0-mm thick sealants (tissue adhesives) were prepared by mixing 200 µl of these adhesive components with 200 µl of that curative component.

The concentration of 4S-PEG was set so that the amount of amino groups in the cGltn or the hydrophobically modified cGltn and the amount of succinimide groups in 4S-PEG might be in a ratio of 1:1.

Then, after the application of each of the sealants (tissue adhesives), crimping was performed for 10 minutes under a load of 5.0 g/mm² and thereby a pressure resistance test was performed. In the pressure resistance test of the sealants (tissue adhesives), the measurement of pressure-resisting strength to a porcine aorta was performed in accordance with ASTM (F2392-04, Standard Test Method for Burst Strength of Surgical Sealants).

(1-2) Result

The results are shown in Table 6.

TABLE 6

|  | Org | 2.1 Hx | 8.5 Hx | 18.3 Hx |
|---|---|---|---|---|
| Average (mmHg) | 96.3 | 246.9 | 233.0 | 202.2 |
| Standard deviation | 9.4 | 12.8 | 11.3 | 9.2 |

Table 6 shows that the cases where the hydrophobically modified cGltn was used as an adhesive component at all of 2.1 Hx, 8.5 Hx, and 18.3 Hx exhibited pressure-resistant strengths being about twice or more the case where the hydrophobically unmodified, Org-cGltn, was used as an adhesive component. Since a high value was exhibited also at 2.1 Hx, a high interface strength with a tissue was believed to be obtained even at a low hydrophobic group introduction ratio.

It has been confirmed regarding cod gelatin that hydrophobically modification was very effective for enhancing bonding strength.

(Example 10) Qualitative Evaluation of Sealant to Rat Organ

A 40% hydrophobically unmodified cGltn was prepared as an adhesive component (Org-cGltn solution), an aqueous solution containing a water-soluble crosslinking agent 4S-PEG was prepared as a curative component (4S-PEG solution), and then a sealant (tissue adhesive) was prepared by mixing this adhesive component with this curative component. This sealant (tissue adhesive) was dropped in an amount of 50 µl to a surface of a rat organ. The sample was left at rest in a 37° C. physiological saline for three days and then was qualitatively evaluated according to the amount of the residual adhesive.

Likewise, a hydrophobically modified cGltn having a hydrophobic group introduction ratio of 2.1 mol % was prepared as an adhesive component (2.1 Hx) and then a sealant (tissue adhesive) was prepared by mixing this adhesive component with that curative component. This sealant (tissue adhesive) was dropped in an amount of 50 µl to a surface of a rat organ. The sample was left at rest in a 37° C. physiological saline for three days and then was qualitatively evaluated according to the amount of the residual adhesive.

As a result, it was revealed that the bonding properties especially to a lung surface and a kidney surface were improved by the use of the hydrophobically modified cGltn (2.1 Hx) as an adhesive component. In contrast, almost no bonding property to organs were confirmed when an Org-cGltn solution was used as an adhesive component.

(Example 11) Examination of the Influence of Hydrophobic Group Introduction Ratio (1) Experimental Method (1-1) A Chol-cGltn in which a part of amino groups of cod gelatin (cGltn) had been cholesterylized was prepared as an adhesive component (expressed as Org-cGltn solution or Org), an aqueous solution containing a water-soluble crosslinking agent 4S-PEG was prepared as a curative component (4S-PEG solution), and then a sealant (tissue adhesive) was prepared by mixing the adhesive component with the curative component.

Likewise, hydrophobically modified cGltns each having a hydrophobic group introduction ratio of 4.9 mol %, 7.5 mol %, or 12.2 mol % by cholesteryl group were prepared as an adhesive component, and sealants (tissue adhesives) were prepared by mixing these adhesive components with the curative component.

A fresh porcine aortic media was used as an adherend and a sealant (tissue adhesive) was applied to this porcine aortic media. After crimping, the strength when the sealant was peeled in a direction perpendicular to the bonded surface was taken as bonding strength.

(1-2) The Detailed Conditions are as Follows.

Applied force (crimping load) 5.0 g/mm²
Contact time (crimping time) 5 min
Solution pH: 0.1M PBS (pH 8)
NHS ratio in $NH_2$/4S-PEG=1/0.85 (NHS: N-hydroxysuccinimide)
Chol-cGltn, cGltn concentration: 40 w/v %
Control: commercially available GRF glue (2) Results Bonding strength increased with introduction of a cholesteryl group up to 7.5 mol % and then decreased. The maximum bonding strength was 1.5 times higher than unmodified cGltn (Org) and 13.8 times higher than a commercial product. Since the condition of a fracture surface shown in FIG. 29 shows that an adhesive remained on the tissue interface in the case of a 7.5 mol % Chol-cGltn, it has been revealed that the adhesive had an interface adhesion property enhanced by cholesteryl group.

(3) Other Hydrophobic Groups

Under the same conditions as in (1) described above, the influence of hydrophobic group introduction ratio on bonding strength was examined also for a propyl group (Pro), a hexanoyl group (Hx), and a lauryl group (Lau).

The results are shown in Table 7. In Table 7 are also shown the results attained by the above-mentioned cholesteryl group.

TABLE 7

| Sample | Hydrophobic group | Hydrophobic group introduction ratio (mol %) | Bonding strength (kPa) | 4S-PEG conc. (mM) |
|---|---|---|---|---|
| A1 | Original (Org) | 0 | 133.2 | 11 |
| A2 | Cholesteryl group | 4.9 | 168 | 10.461 |
| A3 | (Chol) | 7.5 | 202.5 | 10.175 |
| A4 |  | 12.2 | 144.3 | 9.685 |
| A5 | Propyl group (Pro) | 3.2 | 155.6 | 10.648 |
| A6 |  | 6.4 | 179.6 | 10.296 |
| A7 |  | 13.7 | 175 | 9.504 |
| A8 | Hexanoyl group (Hx) | 2.1 | 145.3 | 10.769 |
| A9 |  | 8.5 | 169.7 | 10.065 |
| A10 |  | 18.3 | 203.6 | 8.987 |
| A11 | Lauryl group (Lau) | 3.8 | 159.2 | 10.582 |
| A12 |  | 9 | 175 | 10.01 |

TABLE 7-continued

| Sample | Hydrophobic group | Hydrophobic group introduction ratio (mol %) | Bonding strength (kPa) | 4S-PEG conc. (mM) |
|---|---|---|---|---|
| A13 | | 19 | 222.7 | 8.91 |
| A14 | Control (GRF glue) | / | 14.6 | / |

As shown in Table 7, it was confirmed regarding cod gelatin that hydrophobic modification by a various types of hydrophobic groups is effective for improving bonding strength. In addition, it was also confirmed that a propyl group (Pro), a hexanoyl group (Hx), and a lauryl group (Lau) each enhance bonding strength depending upon a hydrophobic group introduction ratio.

INDUSTRIAL APPLICABILITY

The tissue adhesive of the present invention and the method for producing the same relate to a tissue adhesive that enhances bonding strength, that is not in a gel state but can be used in its original liquid state, and that eases handling. Therefore, they are applicable in the industrial fields where a tissue adhesive, a tissue sealant, a hemostatic agent, and the like are required, and the like.

REFERENCE SIGNS LIST

11 Hydrophobically modified, fish-derived gelatin
12 Hydrophobic group (Cholesteryl group)
13 Amino group
14 Hydroxychlorin
21 Water-soluble crosslinking reagent
22 Crosslinked part
31, 32 Tissue
41 Tissue adhesive
50 Porcine vascular membrane
51 Media
52 Adventitia
53 Mask
54 Hole
55 Weight
60 Tissue adhesive
62, 63 Supporter

The invention claimed is:

1. A tissue adhesive to be applied to a tissue consisting of:
an adhesive component consisting of a solution of a hydrophobically modified fish-derived gelatin in a phosphate buffer solution (PBS) having a pH of from 6.0 to 8.0; and
a curative component consisting of a solution of a water-soluble crosslinking reagent in a phosphate buffer solution (PBS) having a pH of from 6.0 to 8.0, the curative component being provided for mixture with the adhesive component at the time of applying to a tissue,
wherein the water-soluble crosslinking reagent is pentaerythritol poly(ethylene glycol) ether tetrasuccinimidyl glutarate (4S-PEG).

2. The tissue adhesive according to claim 1, wherein the hydrophobically modified fish-derived gelatin comprises, as its main chain, a fish-derived gelatin in which the number of hydroxyproline per 1000 constitutional amino acids thereof is 90 or less.

3. The tissue adhesive according to claim 1, wherein the hydrophobically modified, fish-derived gelatin comprises Lys and a part of the amino groups of the Lys have been substituted with a hydrophobic group.

4. The tissue adhesive according to claim 1, wherein the hydrophobic groups include one type or a combination of two or more types selected from the group consisting of an ethyl group (2 carbon atoms), a propyl (3 carbon atoms), a butyl group (4 carbon atoms), a pentyl group (5 carbon atoms), a hexanoyl group (6 carbon atoms), a heptanoyl group (7 carbon atoms), an octanoyl group (8 carbon atoms), a nonanoyl group (9 carbon atoms), a decanoyl group (10 carbon atoms), an undecanoyl group (11 carbon atoms), a dodecanoyl group (12 carbon atoms), a tridecanoyl group (13 carbon atoms), a tetradecanoyl group (14 carbon atoms), a pentadecanoyl group (15 carbon atoms), a hexadecanoyl group (16 carbon atoms), a heptadecanoyl group (17 carbon atoms), a stearoyl group (18 carbon atoms), which are saturated fatty acids; an isopropyl (3 carbon atoms), an isobutyl group (4 carbon atoms), an isopentyl group (5 carbon atoms), an isohexanoyl group (6 carbon atoms), an isoheptanoyl group (7 carbon atoms), an isooctanoyl group (8 carbon atoms), an isononanoyl group (9 carbon atoms), an isodecanoyl group (10 carbon atoms), an isoundecanoyl group (11 carbon atoms), an isododecanoyl group (12 carbon atoms), an isotridecanoyl group (13 carbon atoms), an isotetradecanoyl group (14 carbon atoms), an isopentadecanoyl group (15 carbon atoms), an isohexadecanoyl group (16 carbon atoms), an isopalmityl group (16 carbon atoms), an isoheptadecanoyl group (17 carbon atoms), an isostearoyl group (18 carbon atoms), which are branched saturated fatty acids; an oleyl group (18 carbon atoms, one unsaturated carbon atom), a linolenyl group (18 carbon atoms, two unsaturated carbon atoms), an α-linolenyl group (18 carbon atoms, three unsaturated carbon atoms), which are unsaturated fatty acids; and a cholesteryl group, which is a cell membrane component.

5. The tissue adhesive according to claim 1, wherein the hydrophobically modified fish-derived gelatin is derived from tilapia, sea bream, or cod.

6. The tissue adhesive according to claim 1, wherein the molecular weight of the hydrophobically modified, fish-derived gelatin is not less than 50000 and less than 100000.

7. The tissue adhesive according to claim 1, wherein the aqueous solution of the hydrophobically modified, fish-derived gelatin is liquid at normal temperatures.

8. A method for producing the tissue adhesive according to claim 1, comprising:
a step of synthesizing the hydrophobically modified, fish-derived gelatin by adding an organic molecule having a hydrophobic group to a solution comprising the fish-derived gelatin in the presence of amine to substitute a part of the amino groups on a side chain of the fish-derived gelatin, wherein the number of hydroxyproline per 1000 constitutional amino acids thereof is 90 or less,
a step of preparing the adhesive component by dispersing the hydrophobically modified fish-derived gelatin in a phosphate buffer solution (PBS) having a pH of from 6.0 to 8.0, and
a step of preparing the curative component by dispersing a water-soluble crosslinking reagent in a phosphate buffer solution (PBS) having a pH of from 6.0 to 8.0, wherein the water-soluble crosslinking reagent is 4S-PEG.

9. A method for using the tissue adhesive according to claim 1, comprising:
a step of mixing the adhesive component with the curative component.

* * * * *